(12) United States Patent
Sakai et al.

(10) Patent No.: US 11,060,081 B2
(45) Date of Patent: Jul. 13, 2021

(54) SPECIMEN PRETREATMENT APPARATUS, SPECIMEN PRETREATMENT CARTRIDGE, AND SPECIMEN PRETREATMENT METHOD

(71) Applicant: Sysmex Corporation, Kobe (JP)

(72) Inventors: Yasuhiro Sakai, Kobe (JP); Hiroaki Tobimatsu, Kobe (JP); Takeo Saitou, Kobe (JP); Tomoko Ohyama, Kobe (JP); Takanori Maekawa, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 620 days.

(21) Appl. No.: 15/443,837

(22) Filed: Feb. 27, 2017

(65) Prior Publication Data

US 2017/0247682 A1    Aug. 31, 2017

(30) Foreign Application Priority Data

Feb. 29, 2016   (JP) .............................. JP2016-038441

(51) Int. Cl.
*C12N 15/10* (2006.01)
*G01N 35/00* (2006.01)

(52) U.S. Cl.
CPC ..... *C12N 15/1013* (2013.01); *G01N 35/0098* (2013.01)

(58) Field of Classification Search
CPC ..................... G01N 35/0098; C12N 15/1013
See application file for complete search history.

(56) References Cited

U.S. PATENT DOCUMENTS

2006/0039824 A1* 2/2006 Onuma ............... B01L 3/021
                                                              422/67
2007/0077580 A1   4/2007 Ikeda et al.
(Continued)

FOREIGN PATENT DOCUMENTS

JP    2009-512445 A    3/2009
JP    2010-54232 A     3/2010
(Continued)

OTHER PUBLICATIONS

The Japanese Office Action dated Oct. 29, 2019 in a counterpart Japanese patent application No. 2016-038441.
(Continued)

*Primary Examiner* — Shogo Sasaki
(74) *Attorney, Agent, or Firm* — Brinks Gilson & Lione

(57) ABSTRACT

Disclosed is a specimen pretreatment apparatus comprising: a specimen container holder configured to hold a specimen container for containing a plasma specimen; a reagent container holder configured to hold a first reagent container for containing a first reagent including magnetic particles on which a nucleic acid in the plasma specimen is adsorbed; a reaction unit in which a plurality of reaction containers are disposed, the reaction unit being configured to accelerate, in each reaction container, reaction of the plasma specimen and the first reagent; a washing unit in which a washing container is disposed, the washing unit including a magnetic force applying portion configured to apply magnetic force to the washing container; a dispensing unit; and a controller programmed to control the dispensing unit to: dispense the plasma specimen contained in the specimen container and the first reagent into the plurality of reaction containers in the reaction unit; dispense a mix liquid of the plasma specimen and the first reagent from each of the plurality of reaction containers into the washing container; and remove a liquid component from the washing container while the (Continued)

magnetic particles contained in the discharged mix liquid is attracted by the magnetic force applying portion.

14 Claims, 18 Drawing Sheets

(56) References Cited

U.S. PATENT DOCUMENTS

| | | | |
|---|---|---|---|
| 2008/0182301 A1 | 7/2008 | Handique et al. | |
| 2009/0176308 A1 | 7/2009 | Griebel et al. | |
| 2009/0214385 A1* | 8/2009 | Mori | G01N 35/00663 422/63 |
| 2010/0284864 A1* | 11/2010 | Holenstein | B01L 3/5085 422/511 |
| 2012/0045751 A1* | 2/2012 | Boyle | C12Q 1/6806 435/5 |
| 2013/0017535 A1* | 1/2013 | Frey | G01N 35/0099 435/5 |
| 2013/0288259 A1 | 10/2013 | Tajima | |
| 2013/0295597 A1* | 11/2013 | DeWitte | G01N 30/06 435/23 |
| 2015/0024375 A1 | 1/2015 | Dalbert et al. | |
| 2015/0316569 A1* | 11/2015 | Fujita | G01N 35/00584 422/67 |

FOREIGN PATENT DOCUMENTS

| | | |
|---|---|---|
| JP | 2010-533490 A | 10/2010 |
| JP | 2012-247330 A | 12/2012 |
| JP | 2013-535193 A | 9/2013 |
| JP | 6771903 B2 | 10/2020 |
| WO | 2007/050327 A2 | 5/2007 |
| WO | 2012/012779 A2 | 1/2012 |
| WO | 2012/050198 A1 | 4/2012 |
| WO | 2016/020455 A1 | 2/2016 |
| WO | 2016/025057 A1 | 2/2016 |

OTHER PUBLICATIONS

S. Berensmeier, "Magnetic particles for the separation and purification of nucleic acids", Appl Microbiol Biotechnol , vol. 73, 2006, pp. 495-504; Cited in the Japanese Office Action dated Jun. 2, 2020 in a counterpart Japanese patent application.
The Japanese Office Action dated Jun. 2, 2020 in a counterpart Japanese patent application No. 2016-038441.
The Japanese Office Action dated Dec. 22, 2020 in a counterpart Japanese patent application No. 2019-230453.

* cited by examiner

SPECIMEN PRETREATMENT APPARATUS, SPECIMEN PRETREATMENT CARTRIDGE, AND SPECIMEN PRETREATMENT METHOD

CROSS REFERENCE TO RELATED APPLICATIONS

This application claims priority from prior Japanese Patent Application No. 2016-038441, filed on Feb. 29, 2016, entitled "SPECIMEN PRETREATMENT APPARATUS, SPECIMEN PRETREATMENT CARTRIDGE, AND SPECIMEN PRETREATMENT METHOD", the entire content of which is incorporated herein by reference.

FIELD OF THE INVENTION

The present invention relates to specimen pretreatment apparatuses, specimen pretreatment cartridges, and specimen pretreatment methods.

BACKGROUND

When a nucleic acid contained in plasma is to be analyzed, pretreatment for extracting the nucleic acid from the plasma is performed. For example, the pretreatment includes: a step of degrading a protein bound to the nucleic acid to isolate the nucleic acid; a step of causing the isolated nucleic acid to be attached to magnetic particles; a step of washing impurities attached to the magnetic particles; and a step of releasing the nucleic acid from the magnetic particles to extract the nucleic acid. US 2015/024375 discloses an analyzer in which: nucleic acids are extracted from a specimen by use of one reaction container having a capacity of about 1 mL; among the extracted nucleic acids, a nucleic acid derived from a target bacterium or virus is amplified by PCR, and the target nucleic acid is analyzed.

In the analyzer disclosed in US 2015/024375, since nucleic acids are extracted from a small amount of plasma of about 25 µL to 75 µL, one reaction container having a capacity of about 1 mL is used. However, in a case where nucleic acids are to be extracted from a large amount of plasma of not less than 1 mL, if a reaction container having a capacity of about 1 mL is used, a process of extracting nucleic acids from a small amount of plasma has to be performed a plurality of times. Thus, the pretreatment takes time. In particular, in a case where a nucleic acid derived from a cancer cell is extracted to be analyzed, if the progression of the cancer is in an early stage, the extractable amount of the nucleic acid derived from the cancer cell is very small. Therefore, in the pretreatment, the nucleic acid needs to be extracted by use of a large amount of plasma. If the pretreatment is performed on such a large amount of plasma, the time required for the pretreatment is further extended.

In the configuration described in US 2015/024375, one reaction container having a capacity of about 1 mL is used, and thus, a large amount of plasma cannot be processed at one time. In that case, it is conceivable that the large amount of plasma could be processed by use of a reaction container having a large capacity. However, in the cases of babies, infants, and children, it is difficult to collect a large amount of plasma, and thus, nucleic acids need to be extracted from a small amount of plasma. However, if a reaction container having a large capacity is used in such a case, compared with a case where a reaction container having a small capacity is used, there is a risk that the small amount of plasma in the reaction container cannot be completely aspirated. Therefore, there are demands for a technique that can shorten the time required in the pretreatment, and that can handle both a large amount of plasma and a small amount of plasma.

SUMMARY OF THE INVENTION

The scope of the present invention is defined solely by the appended claims, and is not affected to any degree by the statements within this summary.

A first mode of the present invention relates to a specimen pretreatment apparatus. The specimen pretreatment apparatus according to this mode includes: a specimen pretreatment apparatus comprising: a specimen container holder configured to hold a specimen container for containing a plasma specimen; a reagent container holder configured to hold a first reagent container for containing a first reagent including magnetic particles on which a nucleic acid in the plasma specimen is adsorbed; a reaction unit in which a plurality of reaction containers are disposed, the reaction unit being configured to accelerate, in each reaction container, reaction of the plasma specimen and the first reagent; a washing unit in which a washing container is disposed, the washing unit including a magnetic force applying portion configured to apply magnetic force to the washing container; a dispensing unit. The controller programmed to control the dispensing unit to: dispense the plasma specimen contained in the specimen container and the first reagent into the plurality of reaction containers in the reaction unit; dispense a mix liquid of the plasma specimen and the first reagent from each of the plurality of reaction containers into the washing container; and remove a liquid component from the washing container while the magnetic particles contained in the discharged mix liquid is attracted by the magnetic force applying portion.

A second mode of the present invention relates to a specimen pretreatment cartridge. The specimen pretreatment cartridge comprising a plurality of reaction containers and a washing container integrally formed therein, the plurality of reaction containers being containers into each of which a plasma specimen and a reagent are dispensed, the reagent including magnetic particles on which a nucleic acid in the plasma specimen is adsorbed, the washing container being a container into which a mix liquid whose reaction in each reaction container has been completed is dispensed in order to remove a liquid component in the mix liquid, the mix liquid including the plasma specimen and the reagent.

A third mode of the present invention relates to a specimen pretreatment method. The specimen pretreatment method comprising: dispensing a plasma specimen contained in a specimen container into a plurality of reaction containers; dispensing, into each reaction container into which the plasma specimen has been dispensed, a reagent which contains magnetic particles on which a nucleic acid in the plasma specimen is adsorbed; heating the reaction container into which a mix liquid of the plasma specimen and the reagent has been dispensed; dispensing the sample into a washing container from the reaction container into which the sample has been dispensed; removing a liquid component in the mix sample; and separating the nucleic acid from the magnetic particles to extract the nucleic acid.

DETAILED DESCRIPTION OF THE PREFERRED EMBODIMENTS

The embodiment below is obtained by applying the present disclosure to a specimen pretreatment apparatus for extracting a nucleic acid from a plasma specimen. The specimen pretreatment apparatus of the embodiment extracts DNA in particular. When DNA is extracted by the specimen pretreatment apparatus of the embodiment, then, a gene is detected according to a BEAMing (Bead, Emulsion, Amplification, and Magnetics) method, for example. That is, the specimen pretreatment apparatus of the embodiment performs pretreatment for extracting DNA, before gene detection. The specimen pretreatment cartridge of the embodiment is used in the pretreatment for extracting DNA, before gene detection.

Figure 1:
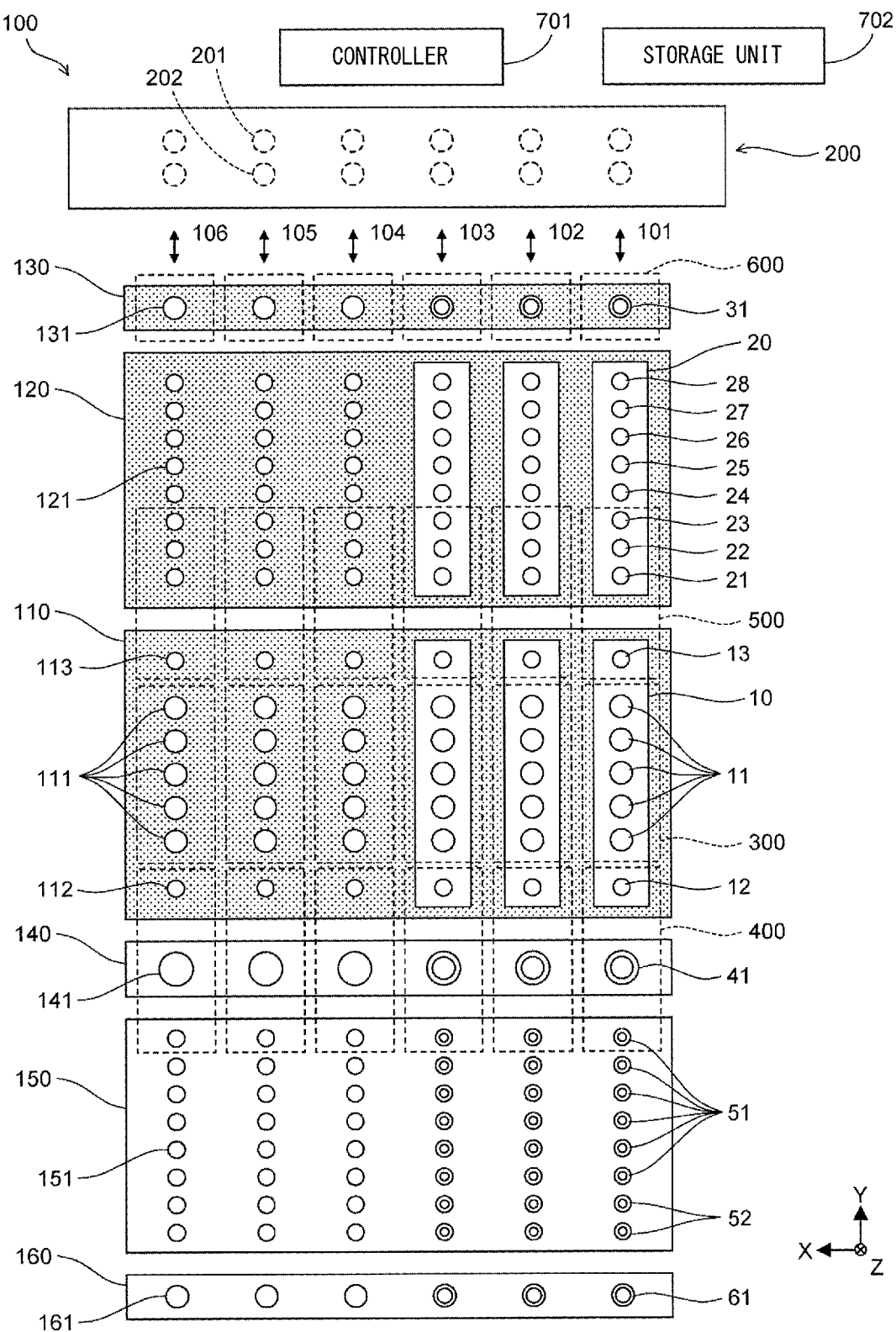
FIG. 1 is a schematic diagram showing a configuration of the inside of a specimen pretreatment apparatus viewed from above according to an embodiment.

As shown in FIG. 1, a specimen pretreatment apparatus 100 includes: plate members 110, 120, 130; holding members 140, 150, 160; a dispensing unit 200; six reaction units 300; six washing units 400; six elution units 500; six cooling units 600; a controller 701; and a storage unit 702. In FIG. 1, the XYZ axes are orthogonal to one another. The X axis positive direction represents the leftward direction, the Y axis positive direction represents the rearward direction, and the Z axis positive direction represents the vertically downward direction. Also in the drawings below, the XYZ axes are the same as the XYZ axes shown in FIG. 1.

Each plate member 110, 120, 130 has holes formed therein as described below. Each holding member 140, 150, 160 has hole-shaped holders formed therein which are recessed relative to the upper face thereof. These holes and holders are arranged along columns 101 to 106 that extend in the Y axis direction. The columns 101 to 106 are arranged in order in the X axis positive direction in the specimen pretreatment apparatus 100. The holes and holders arranged along each column 101 to 106 correspond to the process region for one specimen. Thus, the specimen pretreatment apparatus 100 has six plasma specimen process regions.

In the plate member 110, five holes 111, one hole 112, and one hole 113 are formed along each column 101 to 106. Each hole 111 to 113 penetrates the plate member 110. When one specimen pretreatment cartridge 10 is set, five reaction containers 11, one washing container 12, and one elution container 13 in the specimen pretreatment cartridge 10 are passed through the five holes 111, the one hole 112, and the one hole 113 arranged in the Y axis direction, respectively. Then, the five reaction containers 11 are supported by the reaction unit 300 having hole-shaped holders and disposed below the plate member 110, and the elution container 13 is supported by the elution unit 500 having hole-shaped holders and disposed below the plate member 110. Accordingly, one specimen pretreatment cartridge 10 is set to the plate member 110. Six specimen pretreatment cartridges 10 can be set to the plate member 110 along the columns 101 to 106.

When a process on a plasma specimen is to be started, a new specimen pretreatment cartridge 10 is set in advance at a position in the column, among the columns 101 to 106, where a specimen container 41 is set. The configuration of the specimen pretreatment cartridge 10 will be described later with reference to FIG. 2A.

Figure 2A:
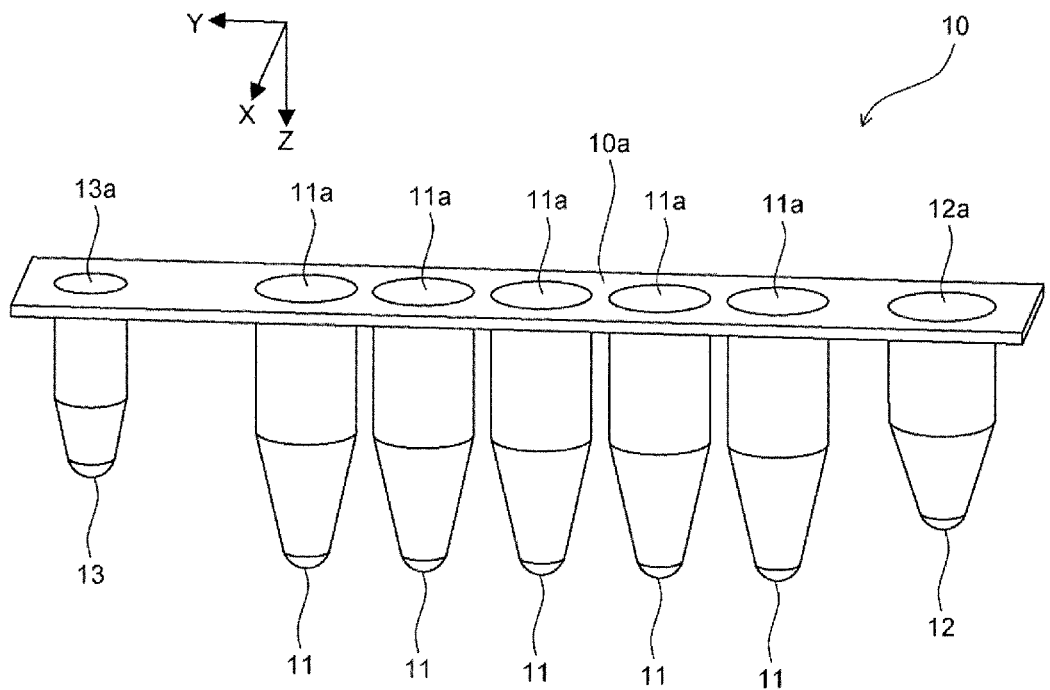
FIG. 2A is a perspective view showing a configuration of a specimen pretreatment cartridge according to the embodiment.

The specimen pretreatment cartridge 10 may be set to the plate member 110 by a flat face portion 10a of the specimen pretreatment cartridge 10 shown in FIG. 2A being supported by the upper face of the plate member 110, instead of the reaction containers 11 and the elution container 13 being supported by the reaction unit 300 and the elution unit 500.

In the plate member 120, eight reagent container holders 121 are formed along each column 101 to 106. Each reagent container holder 121 is a hole provided in the plate member 120. Each reagent container holder 121 penetrates the plate member 120. When one reagent cartridge 20 is set, reagent containers 21 to 28 of the reagent cartridge 20 are passed through to the eight reagent container holders 121 arranged in the Y axis direction, respectively. Then, by a flat face portion 20a of the reagent cartridge 20 shown in FIG. 2B being supported by the upper face of the plate member 120, one reagent cartridge 20 is set to the plate member 120. Six reagent cartridges 20 can be set to the plate member 120 along the columns 101 to 106.

When a process on a plasma specimen is to be started, a reagent cartridge 20 containing reagents is set in advance at a position in the column, among the columns 101 to 106, where a specimen container 41 is set. The reagent containers 21 to 28 of the reagent cartridge 20 contain a solubilizing liquid, a preparation liquid, an extraction liquid, a first reagent, a first washing liquid, a second washing liquid, a third washing liquid, and a second reagent, respectively. The configuration of the reagent cartridge 20 will be described later with reference to FIG. 2B.

In the plate member 130, holes 131 are formed at positions that correspond to the columns 101 to 106, respectively. Each hole 131 penetrates the plate member 130. When a reagent container 31 is to be set, the reagent container 31 is passed through the hole 131. Then, as a result of the reagent container 31 being supported by the cooling unit 600 having a hole-shaped holder and disposed below the plate member 130, the reagent container 31 is set to the plate member 130. Six reagent containers 31 can be set to the plate member 130 at positions that correspond to the columns 101 to 106, respectively. When a process on a plasma specimen is to be started, a reagent container 31 containing a reagent is set in advance at a position in the column, among the columns 101 to 106, where a specimen container 41 is set. The reagent container 31 contains proteinase K. The reagent container 31 containing proteinase K is cooled by the cooling unit 600 until dispensing of proteinase K is performed.

In the holding member 140, hole-shaped specimen container holders 141 are formed at positions that correspond to the columns 101 to 106, respectively. Each specimen container holder 141 holds a specimen container 41. The holding member 140 can hold six specimen containers 41 at positions that correspond to the columns 101 to 106, respectively. When a process on a plasma specimen is to be started, a specimen container 41 containing the plasma specimen is set to a specimen container holder 141 in advance.

In the holding member 150, eight holders 151 are formed along each column 101 to 106. Each holder 151 has a hole shape recessed downwardly from the upper face of the holding member 150. Among the eight holders 151 arranged in the Y axis direction, six holders 151 on the Y axis positive side hold tips 51, respectively, and two holders 151 on the Y axis negative side hold tips 52, respectively. The holding member 150 can hold 36 tips 51 and 12 tips 52 at positions that correspond to the columns 101 to 106. When a process on a plasma specimen is to be started, new tips 51, 52 are set in advance in the holders 151 in the column, among the columns 101 to 106, where a specimen container 41 is set.

In the holding member 160, hole-shaped holders 161 are formed at positions that correspond to the columns 101 to 106, respectively. Each holder 161 holds a container 61. The holding member 160 can hold six containers 61 at positions that correspond to the columns 101 to 106, respectively. When a process on a plasma specimen is to be started, a new container 61 is set in advance in a holder 161 in the column, among the columns 101 to 106, where a specimen container 41 is set.

The dispensing unit 200 includes pairs of nozzles 201 and 202 at positions that correspond to the columns 101 to 106, respectively. The dispensing unit 200 has a configuration for moving the nozzle 201, 202 in the Y axis direction and the Z axis direction. The lower end of the nozzle 201, 202 has a cylindrical shape. When the nozzle 201 is located immediately above a tip 51 held by the holding member 150 and then is lowered, the tip 51 is attached to the lower end of the nozzle 201. Similarly, when the nozzle 202 is located immediately above a tip 52 held by the holding member 150 and then is lowered, the tip 52 is attached to the lower end of the nozzle 202. In addition, the specimen pretreatment apparatus 100 includes a discard portion not shown in which to discard the tip 51, 52 attached to the nozzle 201, 202. When the nozzle 201, 202 is moved in the Y axis direction in a state of being inserted in a hole in the discard portion, the tip 51, 52 is detached from the lower end of the nozzle 201, 202, and the detached tip 51, 52 is collected in the discard portion.

The dispensing unit 200 is configured to be able to dispense a plasma specimen and reagents via the tip 51, 52. In a state where the tip 51, 52 is attached to the nozzle 201, 202, the dispensing unit 200 lowers the lower end of the tip 51, 52 below the liquid surface, and performs aspiration. After performing the aspiration, the dispensing unit 200 moves the lower end of the tip 51, 52 into a discharge target container, and discharges the liquid contained in the tip 51, 52 through the aspiration, into the discharge target container. When discarding the aspirated liquid, the dispensing unit 200 discharges the liquid contained in the tip 51, 52, into a discard portion not shown. The configuration of the dispensing unit 200 will be described later with reference to FIG. 4.

The six reaction units 300 are set below the plate member 110, and are arranged along the columns 101 to 106, respectively. In one reaction unit 300, the five reaction containers 11 of one specimen pretreatment cartridge 10 are disposed. The reaction unit 300 heats the reaction containers 11 disposed therein, to accelerate reaction between the plasma specimen and the reagent contained in each reaction container 11.

The six washing units 400 are set below the plate member 110 and the holding members 140 and 150, and are arranged along the columns 101 to 106, respectively. In one washing unit 400, the washing container 12 of one specimen pretreatment cartridge 10 is disposed. The washing unit 400 performs a process for removing impurities attached to magnetic particles, in the washing container 12 disposed therein.

The six elution units 500 are set below the plate members 110 and 120, and are arranged along the columns 101 to 106, respectively. In one elution unit 500, the elution container 13 of one specimen pretreatment cartridge 10 is disposed. The elution unit 500 performs, in the elution container 13 disposed therein, a process for separating DNA from the magnetic particles and extracting DNA.

The six cooling units 600 are set below the plate member 130, and are arranged at positions that correspond to the columns 101 to 106, respectively. In one cooling unit 600, one reagent container 31 is disposed. The cooling unit 600 cools the reagent container 31 disposed therein to a predetermined temperature.

On the basis of programs stored in the storage unit 702, the controller 701 receives signals from respective components of the specimen pretreatment apparatus 100, and controls the components.

As shown in FIG. 2A, the specimen pretreatment cartridge 10 includes: a flat face portion 10a extending in the Y axis direction; five reaction containers 11; one washing container 12; and one elution container 13. The five reaction containers 11, the one washing container 12, the one elution container 13, and the flat face portion 10a are integrally formed. Specifically, the five reaction containers 11, the one washing container 12, the one elution container 13, the flat face portion 10a are separate components, respectively, and the components are bonded together with an adhesive or the like, whereby the specimen pretreatment cartridge 10 is integrally formed. Other than this, the specimen pretreatment cartridge 10 may be integrally formed by, for example, a resin material such as a plastic being injection-molded so that the five reaction containers 11, the one washing container 12, the one elution container 13, and the flat face portion 10a are integrally mold by the same material. The reaction containers 11, the washing container 12, and the elution container 13 are formed on the lower face side of the flat face portion 10a. In upper portions of the reaction containers 11, the washing container 12, and the elution container 13, openings 11a, 12a, and 13a are formed, respectively. Via the openings 11a, 12a, and 13a, the tip 51, 52 is inserted from above into the reaction containers 11, the washing container 12, and the elution container 13, respectively.

The inner face of each reaction container 11 has the same diameter as the diameter of the opening 11a, from the opening 11a to a predetermined depth position. The inner face of the reaction container 11 has a diameter gradually reduced from this depth position toward the Z axis positive direction, and then is continued to the bottom face recessed in a spherical shape. That is, the reaction container 11 has a cylindrical inner face, a conical inner face, and a bottom face recessed in a spherical shape. The washing container 12 and the elution container 13 each have a cylindrical inner face, a conical inner face, and a bottom face recessed in a spherical shape, similarly to the reaction container 11. The diameter and the depth of the washing container 12 and the elution container 13 are different from those of the reaction container 11. The capacity of the washing container 12 is greater than the capacity of the elution container 13, and the capacity of the reaction container 11 is greater than the capacity of the washing container 12.

Into the reaction container 11, a plasma specimen and reagents for causing a nucleic acid in the plasma specimen to be attached to magnetic particles are dispensed. Into the washing container 12, a sample whose reaction in the reaction container 11 has been completed is dispensed, in order to remove impurities attached to the magnetic particles. Into the elution container 13, the sample for which the process in the washing container 12 has been completed is dispensed, in order to separate DNA in the plasma specimen from the magnetic particles described later.

Since the five reaction containers 11, the one washing container 12, and the one elution container 13 are integrally formed in the specimen pretreatment cartridge 10, these containers can be attached/detached to/from the specimen pretreatment apparatus 100 easily and at the same time.

It should be noted that the five reaction containers 11, the one washing container 12, and the one elution container 13 may be equipped to the specimen pretreatment apparatus 100, in advance. In this case, for each plasma specimen, each container is washed and used. However, in this case, if the plasma specimen remains in the container due to insufficient washing, there is a risk of another plasma specimen being mixed into the plasma specimen that is to be processed. Therefore, in the embodiment, as described above, when a process on a plasma specimen is to be started, a new specimen pretreatment cartridge 10 is set. When the specimen pretreatment cartridge 10 is replaced with a new one for each plasma specimen as described above, compared with a case where a container equipped to the specimen pretreatment apparatus 100 is washed every time to be used, contamination such as another plasma specimen being mixed into the target plasma specimen can be prevented.

The five reaction containers 11 have the same shape with one another. Thus, reaction can be advanced in each of the five reaction containers 11 in a similar manner. The five reaction containers 11 are arranged linearly in one line along the longitudinal direction of the flat face portion 10a. This makes it easy to arrange a plurality of the specimen pretreatment cartridges 10 side by side. Specifically, if the specimen pretreatment cartridges 10 are arranged in a direction that crosses the direction in which the reaction containers 11 are arranged, a plurality of the specimen pretreatment cartridges 10 can be easily set in a compact manner in the specimen pretreatment apparatus 100.

The washing container 12 and the elution container 13 are formed at ends of the specimen pretreatment cartridge 10. This makes it easy to set the washing unit 400 distanced from the reaction containers 11 and the elution container 13 in the specimen pretreatment apparatus 100. Similarly, it is easy to set the elution unit 500 distanced from the reaction containers 11 and the washing container 12 in the specimen pretreatment apparatus 100. In addition, the washing container 12 and the elution container 13 are formed at positions not adjacent to each other. This makes it easy to individually set the washing unit 400 and the elution unit 500 in the specimen pretreatment apparatus 100.

Figure 2B:
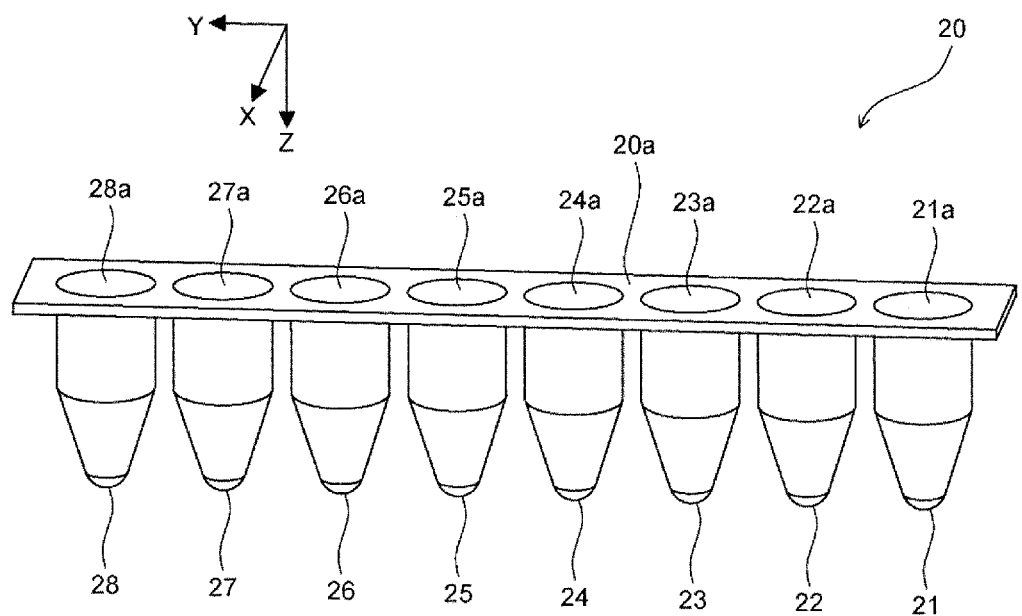
FIG. 2B is a perspective view showing a configuration of a reagent cartridge according to the embodiment.

As shown in FIG. 2B, the reagent cartridge 20 includes: the flat face portion 20a extending in the Y axis direction; and reagent containers 21 to 28. The reagent containers 21 to 28 and the flat face portion 20a are integrally formed. Specifically, the reagent containers 21 to 28 and the flat face portion 20a are separate components, respectively, and the components are bonded together with an adhesive or the like, whereby the reagent cartridge 20 is integrally formed. Other than this, the reagent cartridge 20 may be integrally formed by, for example, a resin material such as a plastic being injection-molded so that the reagent containers 21 to 28 and the flat face portion 20a are integrally molded by the same material. The reagent containers 21 to 28 are formed on the lower face side of the flat face portion 20a, and have the same shape with one another. Similarly to the reaction container 11, each reagent container 21 to 28 has a cylindrical inner face, a conical inner face, and a bottom face recessed in a spherical shape. It should be noted that the reagent containers 21 to 28 may have different shapes from one another, on the basis of the capacity of the reagent to be contained therein. In upper portions of the reagent containers 21 to 28, openings 21a to 28a are formed, respectively. Via the openings 21a to 28a, the tip 51, 52 is inserted from above into the reagent containers 21 to 28, respectively.

As described above, the reagent containers 21 to 28 of the reagent cartridge 20 contain the solubilizing liquid, the preparation liquid, the extraction liquid, the first reagent, the first washing liquid, the second washing liquid, the third washing liquid, and the second reagent, respectively. The preparation liquid, the extraction liquid, and the first reagent are reagents for causing DNA in the plasma specimen to be attached to the magnetic particles. The second reagent is a reagent for releasing the DNA attached to the magnetic particles.

For example, the solubilizing liquid includes Tris-HCl, EDTA-2Na, guanidine thiocyanate, and Tween (registered trademark) 20. The extraction liquid includes Tris-HCl, EDTA-2Na, guanidine thiocyanate, and Tween (registered trademark) 20. The preparation liquid includes isopropanol. The first reagent includes sodium azide, and magnetic particles for causing DNA in the plasma specimen to be attached thereto. The magnetic particles are magnetic particles whose surfaces are coated with silica. The particle forming the magnetic particle is an iron oxide, for example. The first washing liquid includes EDTA-2Na, guanidine hydrochloride, sodium azide, and ethanol. The second washing liquid includes sodium azide and ethanol. The third washing liquid includes ethanol. The second reagent includes Tris-HCl, EDTA-2Na, and sodium azide.

As described above, when a process on a plasma specimen is to be started, a new reagent cartridge 20 containing reagents is set to the column where the plasma specimen is disposed. Thus, the dispensing unit 200 need not have a configuration for moving the nozzle 201, 202 in the X axis direction in order to dispense reagents.

It should be noted that the eight reagents contained in the reagent containers 21 to 28 and the reagent contained in the reagent container 31 may be contained in nine containers equipped to the specimen pretreatment apparatus 100 in advance. In this case, for example, the nine containers are set to the X axis negative side of the holding member 150, and the reagents contained in the respective containers are used in common for the processes performed in the columns 101 to 106. Thus, the dispensing unit 200 needs to have a mechanism for moving the nozzle 201, 202 in the X axis direction. In addition, the setting area in the X axis direction of the specimen pretreatment apparatus 100 is increased. However, since the containers respectively containing the nine reagents are used in common for each plasma specimen, the region in which to dispose the six reagent cartridges 20 and the six reagent containers 31 can be reduced, and thus, the setting area in the Y axis direction of the specimen pretreatment apparatus 100 can be suppressed.

Next, the outline of the flow of the process performed by the specimen pretreatment apparatus 100 will be described with reference to FIG. 1 and FIGS. 3A to 3F.

An operator sets a specimen container 41 containing a plasma specimen to a specimen container holder 141. The operator sets specimen containers 41 to specimen container holders 141 in accordance with the number of plasma specimens to be processed. In the example shown FIG. 1, specimen containers 41 are set to, among the six specimen container holders 141, three specimen container holders 141 at the right side that correspond to the columns 101 to 103, and the process is performed on each of the three plasma specimens.

Via an input unit 704 shown in FIG. 6 described later, the operator inputs an amount of the plasma specimen to be processed, for each specimen container 41 set in the specimen container holder 141. Specifically, via the input unit 704, the operator inputs a value from among 1 mL, 2 mL, 3 mL, 4 mL, and 5 mL for each plasma specimen. The controller 701 obtains the inputted value as information regarding the amount of the plasma specimen (hereinafter, plasma specimen amount information), and stores the obtained plasma specimen amount information in the storage unit 702. Here, the operator causes the specimen container 41 to contain the plasma specimen in advance by an amount not less than the amount inputted for the specimen container 41, and then, sets the specimen container 41 to a specimen container holder 141. Then, the operator inputs via the input unit 704 an instruction for starting the process.

It should be noted that the plasma specimen amount information may be obtained not via the input unit 704. For example, a measurement unit equipped to the dispensing unit 200 aspirates the entire amount of the plasma specimen in the specimen container 41 and measures the aspirated amount, and then, on the basis of the detection signal from the measurement unit, the controller 701 may obtain the plasma specimen amount information. In this case, for example, a value obtained by rounding down the fractions after the decimal point of the amount of the plasma specimen obtained by the dispensing unit 200 is obtained. At this time, if the value obtained by rounding down the fractions after the decimal point is 6 or greater, the value is set to 5. The value thus obtained is used as the plasma specimen amount information.

However, in this example, the plasma specimen amount information is automatically determined in accordance with the amount of the plasma specimen contained in the specimen container 41, and thus, the operator needs to slightly adjust the amount of the plasma specimen to be contained in the specimen container 41 in advance so that the amount of the plasma specimen becomes a desired amount to be processed. Therefore, as in the embodiment, if the plasma specimen amount information can be determined on the basis of the value inputted by the operator, irrespective of the amount of the plasma specimen contained in the specimen container 41, the work of the operator can be simplified.

The plasma specimen amount information may be obtained not via the input unit 704, but by being read from a bar code or an RFID attached to the specimen container 41.

Next, when the start instruction has been inputted, the controller 701 performs in parallel the processes of the plasma specimens contained in the respective specimen containers 41. In the process performed on each plasma specimen, the specimen pretreatment cartridge 10, the reagent cartridge 20, the reagent container 31, the tip 51, 52, and the container 61 are used that are set in the column extending in the Y axis direction with respect to the specimen container 41 containing this plasma specimen.

The controller 701 reads out the plasma specimen amount information stored in the storage unit 702, and controls the dispensing unit 200 so as to dispense the plasma specimen contained in the specimen container 41, the reagents contained in the reagent cartridge 20, and the reagent contained in the reagent container 31, into the reaction containers 11 that are used by the number corresponding to the plasma specimen amount information. Specifically, when 1 mL, 2 mL, 3 mL, 4 mL, or 5 mL has been inputted as the amount of the plasma specimen to be processed, the plasma specimen and the reagents are dispensed into one, two, three, four, or five reaction containers 11.

For example, in a case of a plasma specimen for which 5 mL has been inputted as the amount to be processed, the plasma specimen and the reagents are dispensed into five reaction containers 11 disposed in the same column as this plasma specimen. In a case of a plasma specimen for which 3 mL has been inputted as the amount to be processed, the plasma specimen and the reagents are dispensed into three reaction containers 11 disposed in the same column as this plasma specimen. In a case where three reaction containers 11 are used, among the five reaction containers 11 arranged in the column direction, the three reaction containers 11 on the Y axis negative side are used, and the two reaction containers 11 on the Y axis positive side are not used.

The capacity of each of the five reaction containers 11 is set to a capacity appropriate for causing the dispensed plasma specimen and reagents to efficiently react with one another in a short time. That is, the capacity of each reaction container 11 is set such that: each reagent can be dispensed at a predetermined proportion relative to the plasma specimen dispensed in the reaction container 11; and the plasma specimen and the reagents contained in the reaction container 11 can be quickly heated to a predetermined temperature to accelerate the reaction.

Hereinafter, for convenience, a process on the plasma specimen for which 5 mL has been inputted as the amount to be processed will be described. The dispensing process below is performed by the dispensing unit 200 controlled by the controller 701.

Figure 3A:
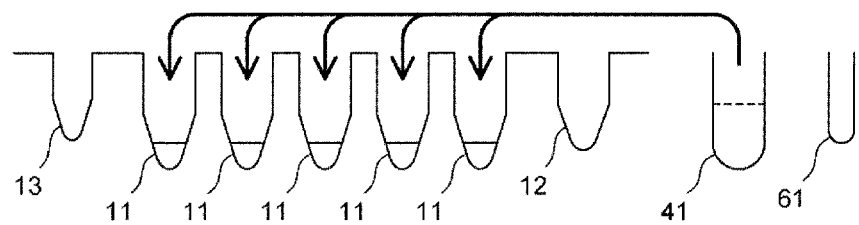
FIG. 3A is a diagram for describing the flow of a process performed by the specimen pretreatment apparatus according to the embodiment.

First, proteinase K contained in the reagent container 31 is dispensed into five reaction containers 11. Into each reaction container 11, an equal amount of proteinase K is dispensed. Subsequently, as shown in FIG. 3A, the plasma specimen contained in the specimen container 41 is dispensed into the five reaction containers 11. Into each reaction container 11, an equal amount of the plasma specimen is dispensed. Specifically, 1 mL of the plasma specimen is dispensed into each of the five reaction containers 11.

Figure 3B:
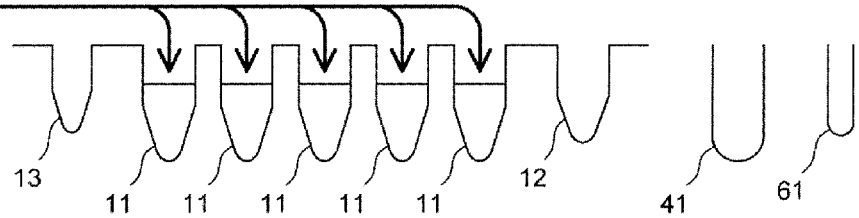
FIG. 3B is a diagram for describing the flow of the process performed by the specimen pretreatment apparatus according to the embodiment.

Subsequently, as shown in FIG. 3B, the solubilizing liquid, the preparation liquid, the extraction liquid, and the first reagent contained in the reagent cartridge 20 are dispensed into the five reaction containers 11. Into each reaction container 11, equal amounts of the reagents are dispensed, respectively, and DNA in the plasma specimen attaches to the magnetic particles.

Figure 3C:
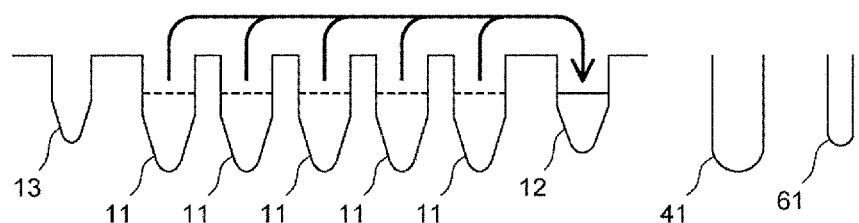
FIG. 3C is a diagram for describing the flow of the process performed by the specimen pretreatment apparatus according to the embodiment.
Figure 3D:
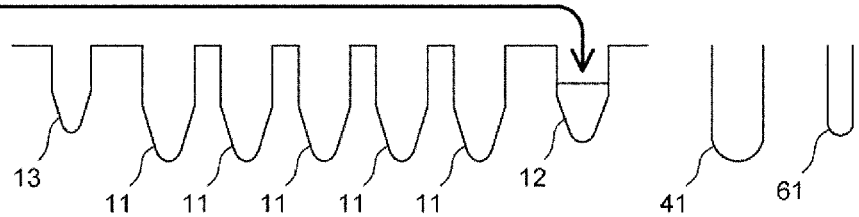
FIG. 3D is a diagram for describing the flow of the process performed by the specimen pretreatment apparatus according to the embodiment.

Subsequently, as shown in FIG. 3C, a predetermined amount of the sample is dispensed from the respective reaction containers 11 in order, into the washing container 12, and impurities contained in the sample are removed as a liquid component. Further, after the sample in all the reaction containers 11 has been dispensed into the washing container 12, the first to third washing liquids contained in the reagent cartridge 20 are dispensed into the washing container 12 as shown in FIG. 3D, and impurities contained in the sample in the washing container 12 are removed as a liquid component.

Figure 3E:
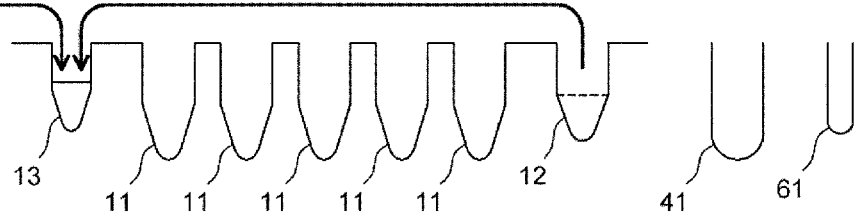
FIG. 3E is a diagram for describing the flow of the process performed by the specimen pretreatment apparatus according to the embodiment.
Figure 3F:
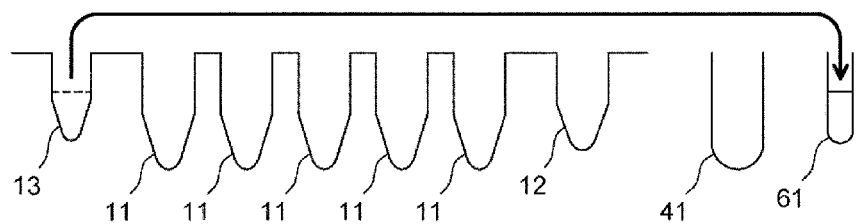
FIG. 3F is a diagram for describing the flow of the process performed by the specimen pretreatment apparatus according to the embodiment.

Subsequently, as shown in FIG. 3E, the sample in the washing container 12 and the second reagent contained in the reagent cartridge 20 are dispensed into the elution container 13, whereby the magnetic particles and DNA are separated from each other. Subsequently, in a state where magnetic force is applied to the elution container 13, the supernatant in the elution container 13 is dispensed into the container 61 as shown in FIG. 3F. The sample in the container 61 includes the extracted DNA. Thus, the process on one plasma specimen is completed. The processes on other plasma specimens are also performed in parallel in the same manner.

When an amount other than 5 mL has been inputted as the amount of the plasma specimen to be processed, the number of reaction containers 11 to be used in the process is changed in accordance with the inputted amount of the plasma specimen. For example, when 3 mL has been inputted as the amount of the plasma specimen to be processed, the plasma specimen is dispensed by 1 mL into each of three reaction containers 11. In addition, the above-described reagents are dispensed into these three reaction containers 11.

In this manner, the plasma specimen and the reagents are dispensed into the reaction containers 11 that are used by the number corresponding to the amount of the plasma specimen, and then, in the respective reaction containers 11 having the plasma specimen and the reagents dispensed therein, reactions with the plasma specimen occur in parallel. That is, when the amount of the plasma specimen is large, e.g., 5 mL, five reaction containers 11 are used, and when the amount of the plasma specimen is small, e.g., 1 mL, one reaction container 11 is used.

Therefore, compared with a case where the plasma specimen to be processed and the reagents are dispensed at one time into one reaction container having a large capacity, the time required in the reaction between the plasma specimen and the reagents can be shortened. In addition, when reaction occurs in a reaction container having a large capacity, the progress degree of the reaction varies depending on the amount of the plasma specimen, which makes it difficult to stably extract DNA. However, when reaction occurs in the reaction containers 11 that are used by the number corresponding to the amount of the plasma specimen as described above, DNA can be stably extracted, irrespective of the amount of the plasma specimen.

In addition, the number of reaction containers 11 into which the plasma specimen is dispensed is determined in accordance with the amount of the plasma specimen. Thus, in the range of the total volume that can be contained in all the reaction containers 11, i.e., up to 5 mL in the embodiment, the plasma specimen can be processed at one time. Therefore, the specimen pretreatment apparatus 100 of the embodiment can shorten the time required in the pretreatment for extracting DNA, and can handle both a large amount of a plasma specimen and a small amount of a plasma specimen.

As described above, the plasma specimen is evenly distributed by 1 mL from the specimen container 41 into each reaction container 11. That is, an equal amount of the plasma specimen is dispensed into each reaction Container 11. Accordingly, compared with a case where the plasma specimen to be processed is unevenly dispensed into the respective reaction container 11, the time required until the reaction ends in all the reaction containers 11 can be shortened.

Furthermore, the reaction advances almost evenly in the respective reaction container 11.

The controller 701 may receive a value other than an integer value as the information regarding the amount of the plasma specimen to be processed. In this case, the number of reaction containers 11 into which the plasma specimen is to be dispensed, and the amount of the plasma specimen to be dispensed may be determined such that the amount of the plasma specimen to be dispensed into each reaction container 11 is close to 1 mL. For example, when 3.6 mL has been inputted, 0.9 mL of the plasma specimen may be dispensed in each of four reaction containers 11. When 4.4 mL has been inputted, 1.1 mL of the plasma specimen may be dispensed into each of four reaction containers 11. Further, as long as no big difference is caused between the reactions in the respective reaction containers 11, different amounts of the plasma specimen may be dispensed in the respective reaction containers 11. For example, when 3.6 mL has been inputted, 1 mL, 1 mL, 0.8 mL, and 0.8 mL of the plasma specimen may be dispensed into four reaction containers 11, respectively.

The controller 701 may receive an amount smaller than 1 mL as the information regarding the amount of the plasma specimen to be processed. In this case, the plasma specimen is dispensed by the received amount into only one reaction container 11. Accordingly, a further smaller amount of the plasma specimen can be handled.

In the embodiment, the specimen pretreatment cartridge 10 includes five reaction containers 11, but not limited thereto, may include two to four, or six or more reaction containers 11.

Figure 4:
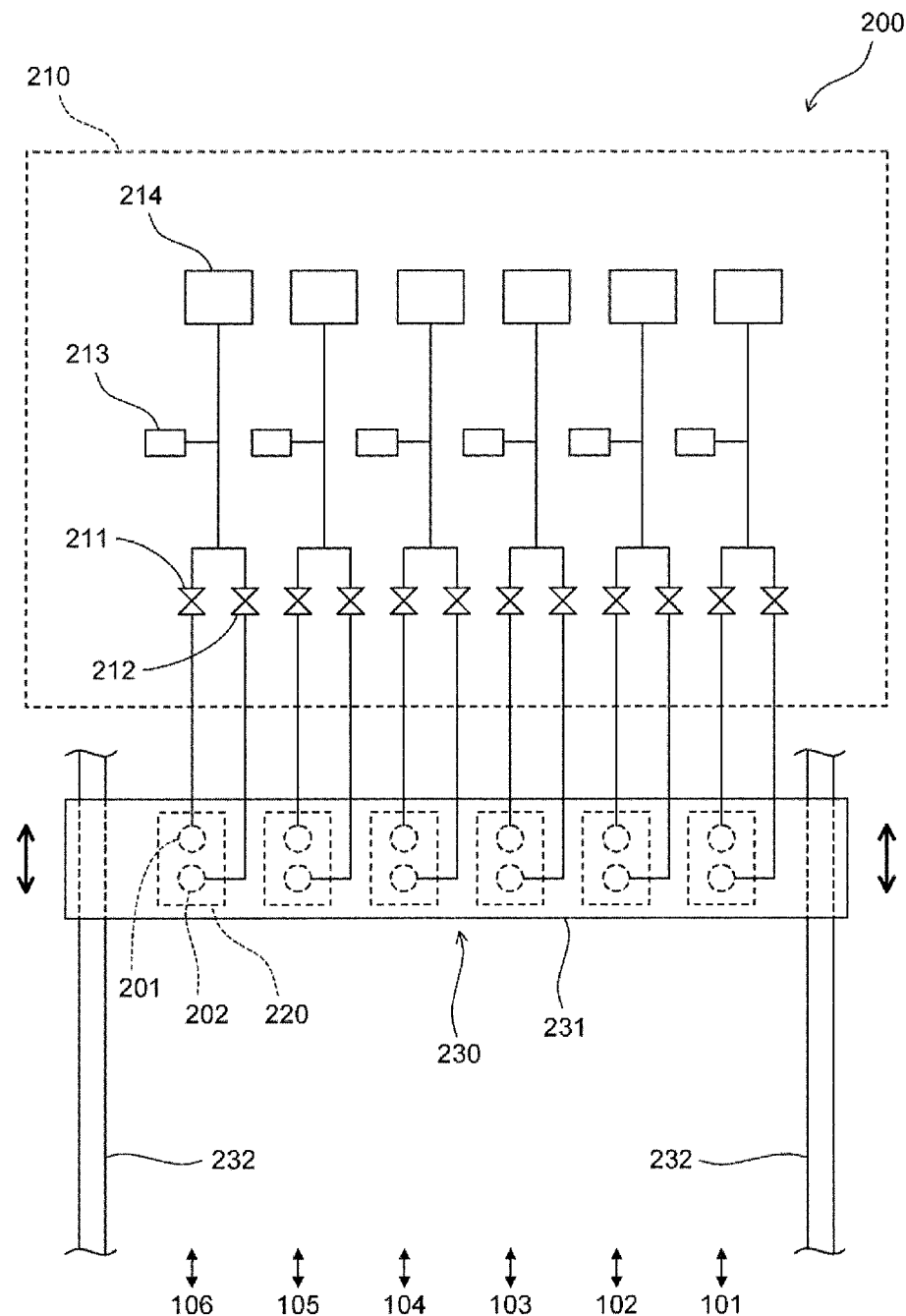
FIG. 4 is a schematic diagram showing a configuration of a dispensing unit viewed from above according to the embodiment.

As shown in FIG. 4, the dispensing unit 200 includes: the nozzles 201, 202; a pressure applying unit 210; six up-down transferring units 220; and a front-rear transferring unit 230.

The pressure applying unit 210 includes: six valves 211; six valves 212; six pressure sensors 213; and six pumps 214. When the valve 211 is opened and the valve 212 is closed, if the pump 214 is driven, liquid dispensing is enabled via the tip 51 attached to the nozzle 201. When the valve 211 is closed and the valve 212 is opened, if the pump 214 is driven, liquid dispensing is enabled via the tip 52 attached to the nozzle 202. The pressure sensor 213 detects the pressure in the passage connecting the pump 214 and the valves 211, 212 together.

The six up-down transferring units 220 are set to the lower face side of a support portion 231, so as to correspond to the nozzles 201, 202 provided along the columns 101 to 106. Each up-down transferring unit 220 includes a motor not shown, and transfers the pair of the nozzles 201 and 202 arranged in the column direction, in the up-down direction by being driven by the motor. The six up-down transferring units 220 can be individually driven. Accordingly, it is possible to individually dispense the plasma specimen and the reagents disposed in the columns 101 to 106. The front-rear transferring unit 230 includes the support portion 231 and two rails 232. The front-rear transferring unit 230 includes a motor not shown, and transfers the support portion 231 in the Y axis direction along the rails 232, by being driven by the motor.

When a liquid is to be aspirated, the controller 701 controls the dispensing unit 200 so as to lower the tip 51, 52 from above the liquid surface. When the lower end of the tip 51, 52 comes into contact with the liquid surface, the pressure changes in the passage connecting the pump 214 and the valve 211, 212 together. On the basis of the change in the detection signal from the pressure sensor 213, the controller 701 detects that the lower end of the tip 51, 52 has come into contact with the liquid surface. Then, the controller 701 controls the dispensing unit 200 so as to move the nozzle 201, 202 downward in accordance with a dispensing amount, and aspirate a predetermined amount of the liquid via the tip 51, 52. When a liquid is to be discharged, the controller 701 controls the dispensing unit 200 such that the lower end of the tip 51, 52 is located in the discharge target container. Then, the controller 701 controls the dispensing unit 200 so as to discharge the liquid in the tip 51, 52.

Figure 5:
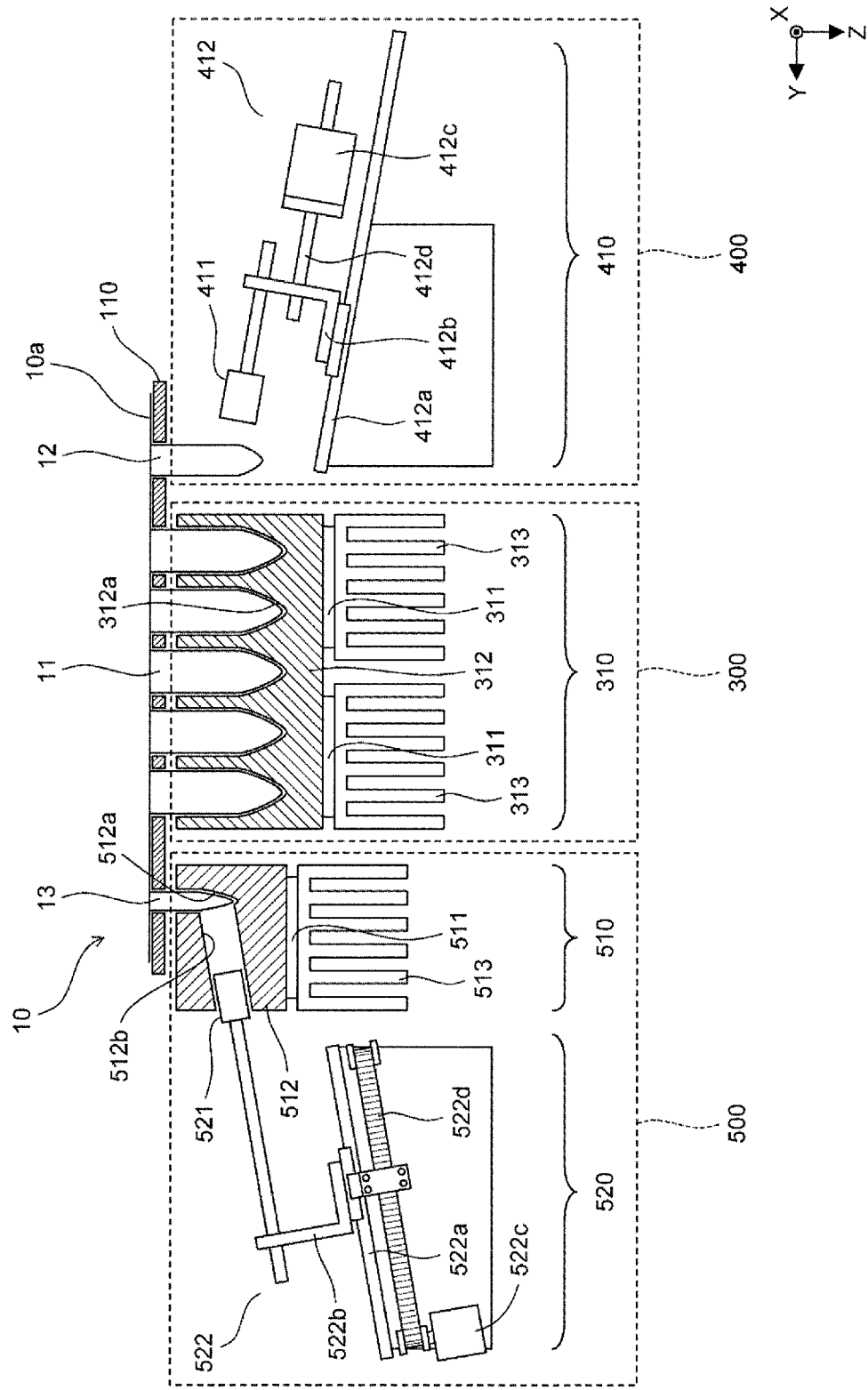
FIG. 5 shows configurations of a reaction unit, a washing unit, and an elution unit according to the embodiment.

With reference to FIG. 5, configurations of the reaction unit 300, the washing unit 400, and the elution unit 500 will be described. FIG. 5 shows cross sections of the specimen pretreatment cartridge 10, the plate member 110, and conductive members 312 and 512, taken along a plane that is parallel to the Y-Z plane and that passes the center position in the X axis direction of the specimen pretreatment cartridge 10. As to the other configurations, external views when viewed in the X axis negative direction are shown for convenience.

The reaction unit 300 includes a heating portion 310 which heats the reaction containers 11. The heating portion 310 includes: two heaters 311; a conductive member 312; and two heat dissipating members 313. The two heaters 311 are set to the lower face of the conductive member 312, and heat the five reaction containers 11 by heating the conductive member 312. Instead of the heaters 311, Peltier elements may be used.

The conductive member 312 is formed from a metal having a high thermal conductivity, and conducts heat of the heaters 311 to the reaction containers 11. The two heat dissipating members 313 are set to the lower faces of the two heaters 311, respectively, and efficiently dissipate heat of the heaters 311 and the conductive member 312 after heating by the heaters 311 ends. The conductive member 312 includes five reaction container holders 312a for holding the five reaction containers 11, respectively. The five reaction container holders 312a are each formed in a circular hole shape recessed from the upper face of the conductive member 312. The diameter of each reaction container holder 312a is substantially the same as the diameter of the reaction container 11. The inner face of the reaction container holder 312a has a shape that allows the outer face of the reaction container 11 to fit therein.

The washing unit 400 includes a magnetic force applying portion 410 which applies magnetic force to the washing container 12. The magnetic force applying portion 410 includes a magnet 411 and a magnet driving portion 412 which moves the magnet 411. The magnet driving portion 412 includes a rail 412a, a moving member 412b, a motor 412c, and a driving shaft 412d. The moving member 412b is formed so as to be movable along the rail 412a. The magnet 411 is set via a bar-shaped member to the moving member 412b. The motor 412c is fixed in the specimen pretreatment apparatus 100. One end of the driving shaft 412d is connected to the shaft of the motor 412c. The driving shaft 412d has a thread groove formed therein. The thread groove of the driving shaft 412d is connected to a screw hole formed in the moving member 412b.

As shown in FIG. 5, when the specimen pretreatment cartridge 10 is set, the washing container 12 is located below the hole 112 shown in FIG. 1 via the flat face portion 10a. When the motor 412c is driven in this state, the magnet 411 is moved between a position near the bottom of the washing container 12 and a position far from the bottom of the washing container 12, via the moving member 412b and the driving shaft 412d. The rail 412a is disposed such that the Y axis positive side thereof is raised toward the Z axis negative direction relative to the direction parallel to the Y axis. Thus, the magnet 411 is obliquely moved, associated with driving of the motor 412c.

The elution unit 500 includes: a heating portion 510 which heats the elution container 13; and a magnetic force applying portion 520 which applies magnetic force to the elution container 13. The heating portion 510 includes a heater 511, a conductive member 512, and a heat dissipating member 513. The heater 511 is set to the lower face of the conductive member 512, and heats the conductive member 512. Instead of the heater 511, a Peltier element may be used.

The conductive member 512 is formed from a metal having a high thermal conductivity, and conducts heat of the heater 511 to the elution container 13. The heat dissipating member 513 is set to the lower face of the heater 511, and efficiently dissipates heat of the heater 511 and the conductive member 512 after heating by the heater 511 ends. The conductive member 512 includes: an elution container holder 512a for holding the elution container 13; and a hole 512b continued to the elution container holder 512a. The elution container holder 512a is formed in a circular hole shape recessed from the upper face of the conductive member 512. The diameter of the elution container holder 512a is substantially the same as the diameter of the elution container 13. The inner face of the elution container holder 512a has a shape that allows the outer face of the elution container 13 to fit therein. The hole 512b is continued to the elution container holder 512a from a side face of the conductive member 512.

The magnetic force applying portion 520 includes a magnet 521 and a magnet driving portion 522 which moves the magnet 521. The magnet driving portion 522 includes a rail 522a, a moving member 522b, a motor 522c, and a belt 522d. The moving member 522b is formed so as to be movable along the rail 522a. The magnet 521 is set via a bar-shaped member to the moving member 522b. The motor 522c is fixed in the specimen pretreatment apparatus 100. The belt 522d is looped over two pulleys. The pulley on the Y axis positive side is connected to the shaft of the motor 522c. The moving member 522b is connected to the belt 522d by a fixture.

As shown in FIG. 5, when the specimen pretreatment cartridge 10 is set, the elution container 13 is held by the elution container holder 512a. When the motor 522c is driven in this state, the magnet 521 is moved along the hole 512b between a position near the bottom of the elution container 13 and a position far from the bottom of the elution container 13, via the moving member 522b and the belt 522d. The rail 522a is disposed such that the Y axis negative side thereof is raised toward the Z axis negative direction relative to the direction parallel to the Y axis. The hole 512b extends in parallel to the rail 522a. Thus, the magnet 521 is obliquely moved, associated with driving of the motor 522c.

When the specimen pretreatment cartridge 10 is set, the five reaction containers 11 passed through the holes 111 in the plate member 110 shown in FIG. 1 are inserted in the reaction container holders 312a to be held by the reaction container holders 312a. In addition, one elution container 13 passed through the hole 113 in the plate member 110 shown in FIG. 1 is inserted in the elution container holder 512a to be held by the elution container holder 512a. As a result, the five reaction containers 11 are disposed at the reaction unit 300, the washing container 12 is disposed at the washing unit 400, and the elution container 13 is disposed at the elution unit 500.

When the specimen pretreatment cartridge 10 is set, it is preferable that the outer face of each reaction container 11 is held without a gap by its corresponding reaction container holder 312a, and that the outer face of the elution container 13 is held without a gap by the elution container holder 512a. Accordingly, the heat generated from the heaters 311 is efficiently conducted via the conductive member 312 to the reaction containers 11, and the heat generated from the heater 511 is efficiently conducted via the conductive member 512 to the elution container 13.

In the embodiment, the reaction unit 300, the washing unit 400, and the elution unit 500 are provided so as to correspond to the specimen pretreatment cartridge 10 which is disposed for each plasma specimen, i.e., so as to correspond to the column 101 to 106. Accordingly, for the respective plasma specimens, the processes using the reaction unit 300, the washing unit 400 and the elution unit 500 can be independently performed. It should be noted that in the reaction unit 300, heaters may be individually provided for the respective five reaction containers 11.

In a case where the processes on plasma specimens in the columns 101 to 106 are synchronously performed with one another, one reaction unit 300, one washing unit 400, and one elution unit 500 may be provided so as to be used in common for the columns 101 to 106. In this case, the heaters 311, 511, the conductive members 312, 512, and the heat dissipating members 313, 513 are extended in the X axis direction so as to correspond to the six specimen pretreatment cartridges 10 disposed in the columns 101 to 106. In addition, the six magnets 411 that correspond to the respective washing containers 12 are driven by a single magnet driving portion 412, and the six magnets 521 that correspond to the respective elution containers 13 are driven by a single magnet driving portion 522.

Figure 6:
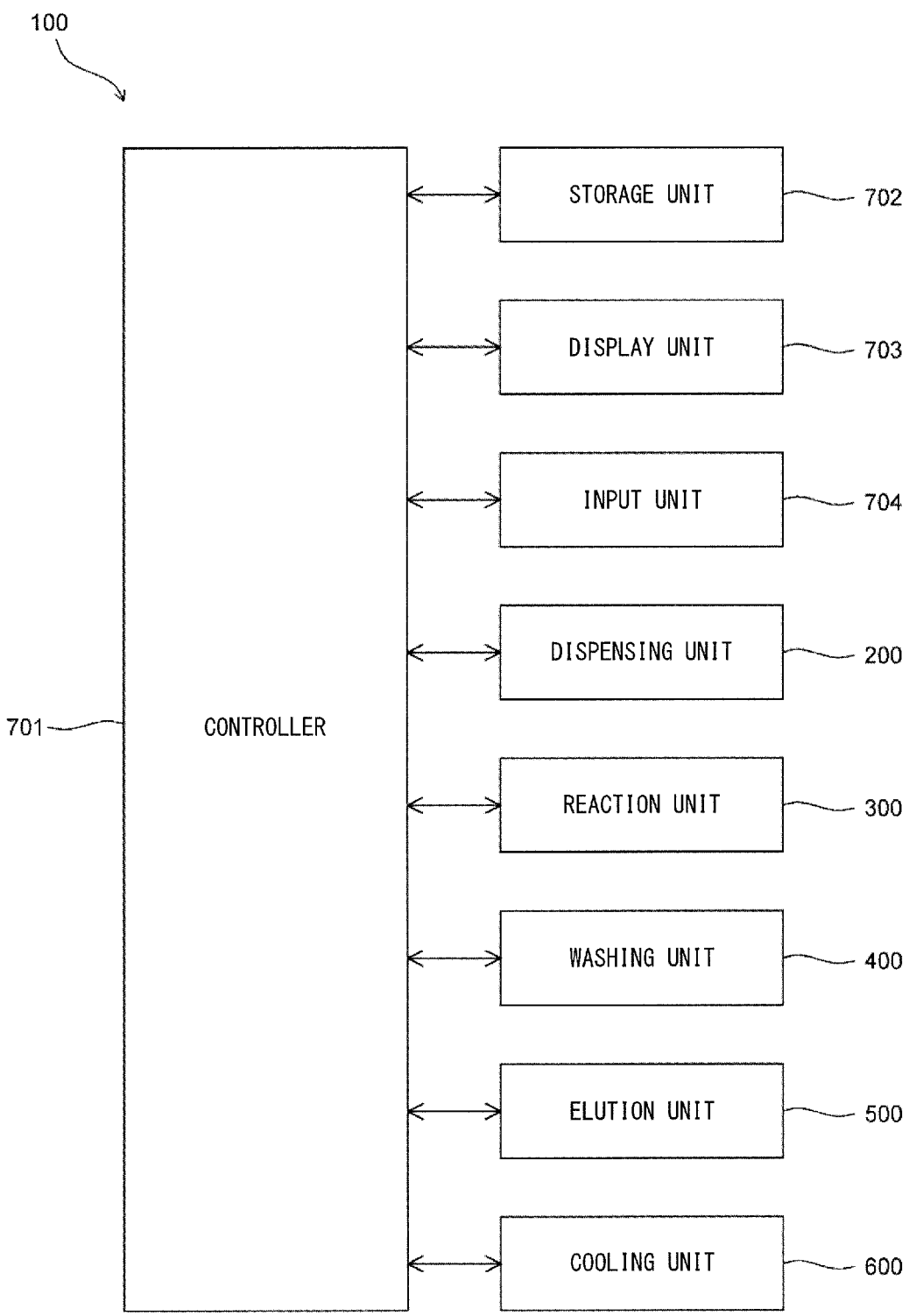
FIG. 6 is a block diagram showing a configuration of the specimen pretreatment apparatus according to the embodiment.

As shown in FIG. 6, the specimen pretreatment apparatus 100 includes the controller 701, the storage unit 702, a display unit 703, the input unit 704, the dispensing unit 200, the reaction unit 300, the washing unit 400, the elution unit 500, and the cooling unit 600.

The controller 701 is implemented by a CPU or a microcomputer. The controller 701 receives signals from components of the specimen pretreatment apparatus 100 and controls the components. The storage unit 702 is implemented by a RAM, a ROM, a hard disk, and the like. The controller 701 may be implemented by a CPU and a microcomputer. In this case, for example, it may be configured such that: the microcomputer controls the components of the specimen pretreatment apparatus 100; and the CPU communicably connected to the microcomputer transmits instruction signals to the microcomputer. That is, the controller 701 may be implemented by a plurality of controllers.

The display unit 703 is implemented by a display. The input unit 704 is implemented by a mouse and a keyboard. The specimen pretreatment apparatus 100 may include a display input unit implemented by a touch panel display, instead of the display unit 703 and the input unit 704.

Next, processes performed by the specimen pretreatment apparatus 100 will be described with reference to flow charts.

Figure 7:
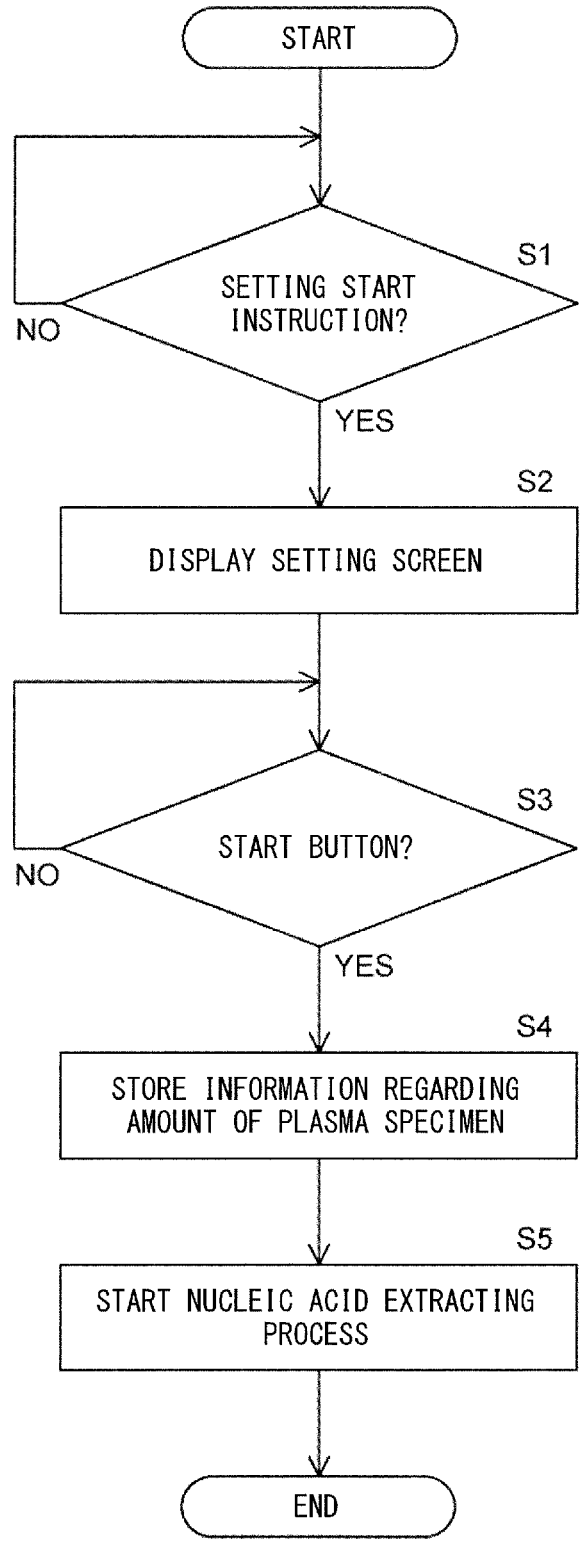
FIG. 7 is a flow chart of a process performed by the specimen pretreatment apparatus for storing plasma specimen amount information and starting a nucleic acid extracting process according to the embodiment.

As shown in FIG. 7, in step S1, the controller 701 determines whether a setting start instruction has been received via the input unit 704 by the operator. When the controller 701 has received the setting start instruction, then, in step S2, the controller 701 displays a setting screen 800 on the display unit 703.

Figure 8:
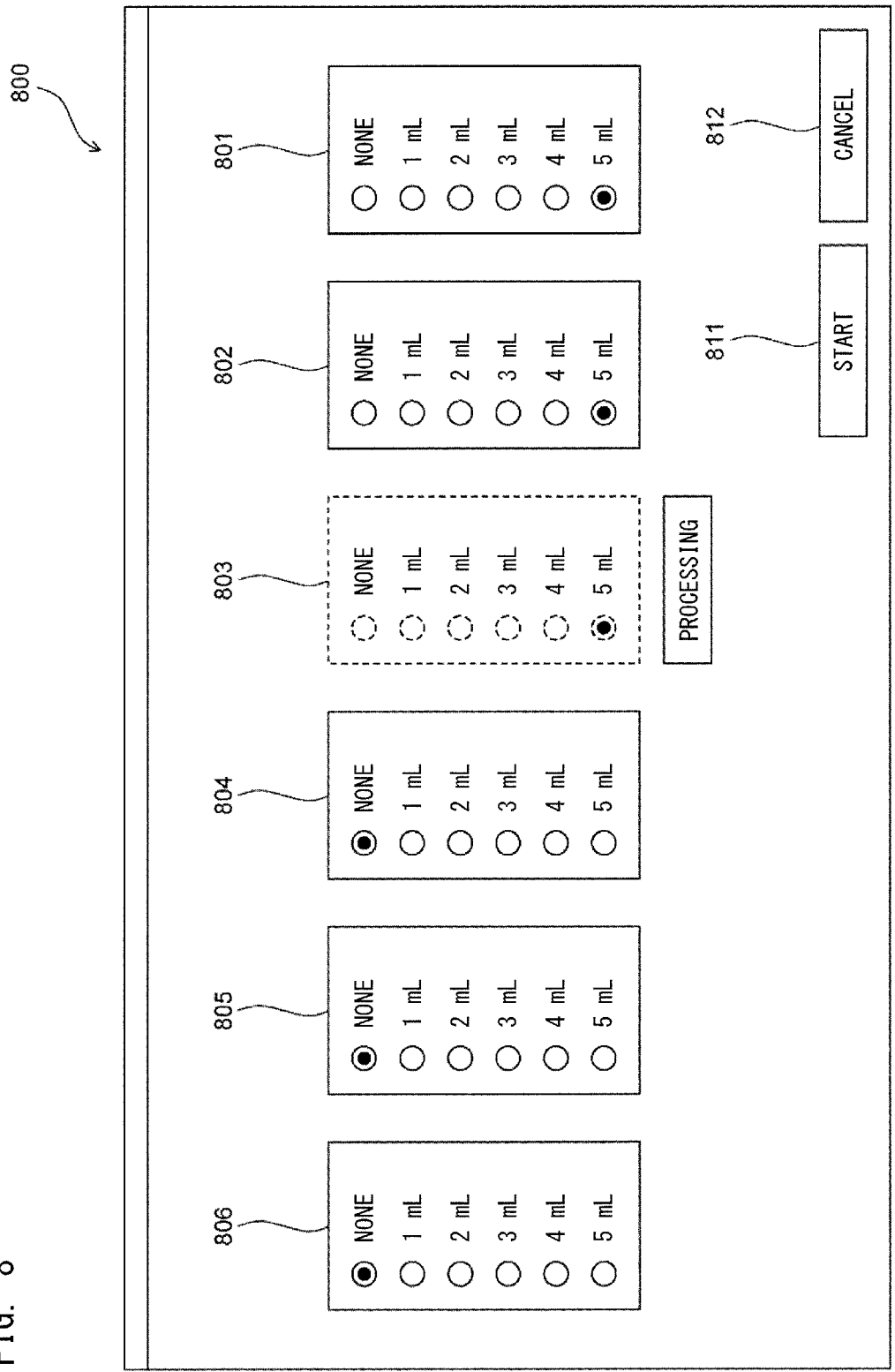
FIG. 8 shows a configuration of a setting screen according to the embodiment.

As shown in FIG. 8, the setting screen 800 includes setting display regions 801 to 806, a start button 811, and a cancel button 812. The setting display regions 801 to 806 respectively include value input portions in which amounts of plasma specimens to be processed in the columns 101 to 106 can be set. In the example shown in FIG. 8, the value input portions are implemented by six radio buttons. The six radio buttons correspond to none, 1 mL, 2 mL, 3 mL, 4 mL, and 5 mL, respectively. In the initial state, the radio button that corresponds to "none" is selected. The value input portion of each setting display region 801 to 806 is not limited to the radio button as mentioned above, but may be implemented by a list box, a text box, or the like which allows setting of an amount of a plasma specimen.

In the setting display region that corresponds to the column in which a specimen container 41 has been set, the operator sets an amount of the plasma specimen to be processed in the plasma specimen contained in this specimen container 41, by selecting a radio button via the input unit 704. Then, the operator presses the start button 811 via the input unit 704, to start a nucleic acid extracting process performed by the specimen pretreatment apparatus 100. At this time, with respect to any column for which "none" is set, the controller 701 does not start the process. When cancelling the setting in the setting display region 801 to 806 and closing the setting screen 800, the operator presses the cancel button 812 via the input unit 704.

It should be noted that, when the setting screen 800 is displayed while the nucleic acid extracting process is being performed, the setting display region that corresponds to the column for which the process is being performed is in a state of not receiving any input. For example, when the process on the plasma specimen that corresponds to the column 103 is already being performed, the setting display region 803 is in a state of not receiving any input as indicated by the dashed line, and "processing" which indicates that the process is being performed is displayed below the setting display region 803, as in the example shown in FIG. 8. Even when there is a column for which the process is being performed, if there is a column for which the process is not being performed, an input for that column for which the process is not being performed can be received. When the operator selects via the input unit 704 an amount of the plasma specimen in a setting display region capable of receiving an input, and presses the start button 811, the nucleic acid extracting process that corresponds to the set column is started. Any process that is started later is performed in parallel with the nucleic acid extracting process that is already being performed.

With reference back to FIG. 7, in step S3, the controller 701 determines whether the start button 811 has been pressed via the input unit 704 by the operator. When the controller 701 has determined that the start button 811 has been pressed, then, in step S4, the controller 701 stores plasma specimen amount information into the storage unit 702, on the basis of the setting display region 801 to 806. It should be noted that, in step S4, when a value from among 1 mL to 5 mL has been set in a setting display region that corresponds to a column for which the process is not being performed, the plasma specimen amount information is stored on the basis of this setting display region. Then, in step S5, the controller 701 starts the nucleic acid extracting process for the plasma specimen whose plasma specimen amount information has been stored.

Figure 9:
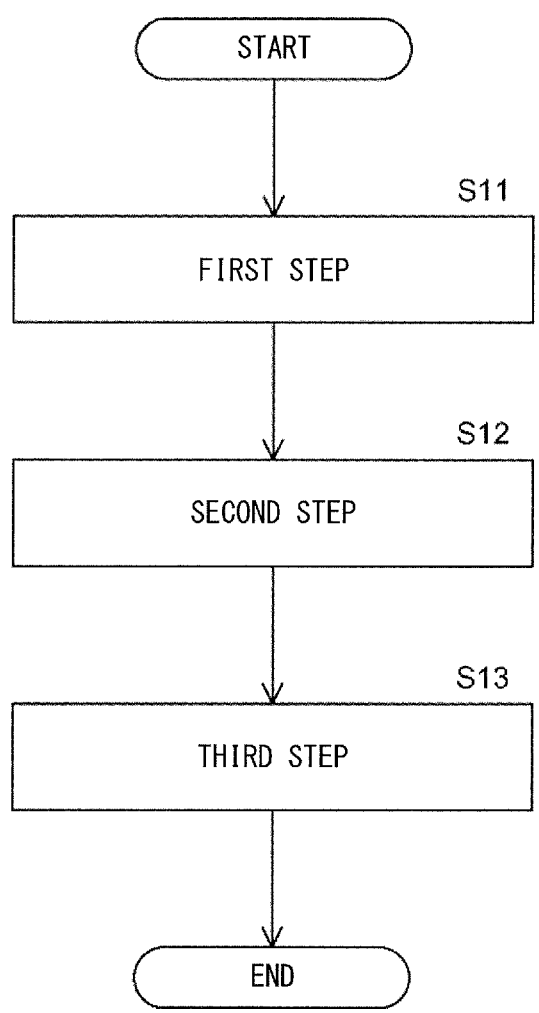
FIG. 9 is a flow chart showing the nucleic acid extracting process according to the embodiment.

As shown in FIG. 9, in the nucleic acid extracting process, the controller 701 performs a first step of step S11, a second step of step S12, and a third step of step S13 in order. The processes of steps S11 to S13 are performed for each plasma specimen. Details of each step will be described later with reference to FIG. 11 to FIG. 17. Here, before the detailed description of each step is given, how DNA is extracted from a plasma specimen through the steps will be described.

Figure 10A:
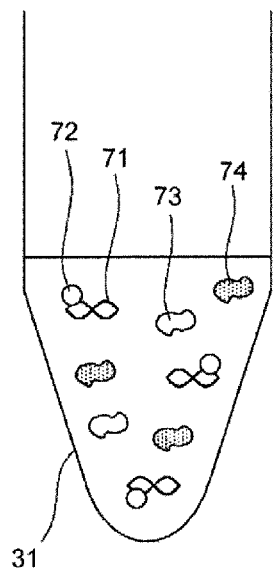
FIGS. 10A to 10F are diagrams for describing how DNA is extracted from plasma specimen through first to third processes according to the embodiment.

As shown in FIG. 10A, the plasma specimen in the specimen container 41 includes: a DNA 71; a histone 72 which is a DNA binding protein that binds to DNA in the plasma specimen; an enzyme 73 which degrades the DNA 71; a protein in plasma specimen (hereinafter, plasma specimen protein) 74; and the like. In the first step, proteinase K is dispensed into a reaction container 11, the plasma specimen in the specimen container 41 is dispensed in to the reaction container 11, and the solubilizing liquid is dispensed into the reaction container 11. Proteinase K degrades the histone 72 binding to the DNA 71, to separate the histone 72 from the DNA 71. Furthermore, proteinase K degrades the enzyme 73, to suppress the activity of the enzyme 73. Other than this, proteinase K degrades the plasma specimen protein 74. The solubilizing liquid creates an environment in which proteinase K can easily act.

Subsequently, the preparation liquid and the extraction liquid are dispensed into the reaction container 11. Since the DNA 71 is highly hydrophilic, the DNA 71 easily forms a hydrogen bond with a water molecule in a solution. On the other hand, silica coating the surface of a magnetic particle 77 shown in FIG. 10C is highly hydrophobic. Therefore, the DNA 71 in the initial state is less likely to bind to silica on the magnetic particle 77. The preparation liquid removes the water molecule bonded to the DNA 71 to make the DNA 71 hydrophobic. This allows the hydrophobic DNA 71 to attach silica on the magnetic particle 77. The extraction liquid creates an environment that allows the DNA 71 to attach to the magnetic particle 77. In the first step, when reaction advances in the reaction container 11, the inside of the reaction container 11 exhibits the state shown in FIG. 10B, for example.

Figure 10B:
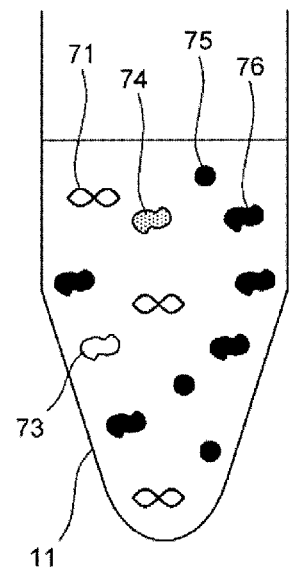
Figure 10C:
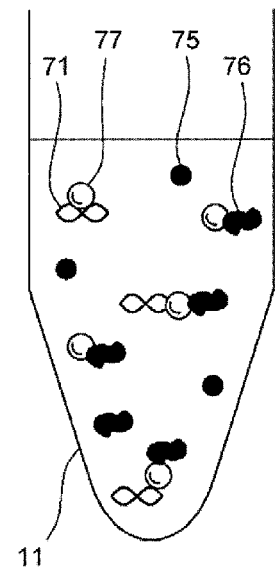

As shown in FIG. 10B, the sample in the reaction container 11 at this time includes the DNA 71, the enzyme 73, the plasma specimen protein 74, denatured substances 75, 76, and the like. The denatured substance 75 is the histone 72 having been denatured and degraded. The denatured substance 76 is the enzyme 73 and the plasma specimen protein 74 that have been denatured and degraded. When reaction advances in the reaction container 11, the histone 72 is separated from the DNA 71, and the histone 72, the enzyme 73, and the plasma specimen protein 74 are denatured and degraded. Further, in the first step, the first reagent containing the magnetic particles is dispensed into the reaction container 11. Accordingly, the DNA 71 attaches to the magnetic particle 77 and the inside of the reaction container 11 exhibits the state shown in FIG. 10C, for example. It should be noted that the denatured substances 75, 76, and the like in the plasma specimen also attach to the magnetic particles 77.

Figure 10D:
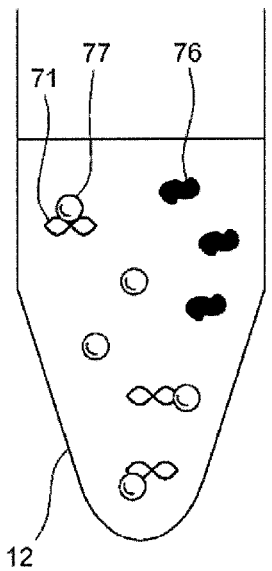

In the second step, the sample in the reaction container 11 is dispensed into the washing container 12, and the magnetic particles 77 are attached to the inner wall of the washing container 12 by the magnet 411 of the washing unit 400 shown in FIG. 5. Then, the supernatant liquid is removed from the washing container 12. As a result, the denatured substances 75, 76 that are not bound to the magnetic particles 77 in the plasma specimen are removed. Subsequently, the first washing liquid is dispensed into the washing container 12. Accordingly, the denatured substances 75, 76 bound to the magnetic particles 77 are separated, and the inside of the washing container 12 exhibits the state shown in FIG. 10D, for example. Then, the supernatant liquid is removed from the washing container 12 by use of the magnet 411, whereby the denatured substances 75, 76 are removed from the sample. Subsequently, the second washing liquid is dispensed into the washing container 12. Then, the supernatant liquid is removed from the washing container 12 by use of the magnet 411, whereby the denatured substances 75, 76 are further removed from the sample.

Subsequently, the third washing liquid is dispensed into the washing container 12. Then, the sample in the washing container 12 is dispensed into the elution container 13, and the magnetic particles 77 are attached to the inner wall of the elution container 13 by the magnet 521 of the elution unit 500 shown in FIG. 5. Then, the supernatant liquid is removed from the elution container 13, whereby the denatured substances 75, 76 are further removed from the sample.

Figure 10E:
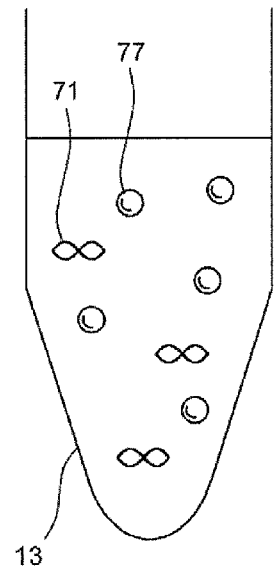
Figure 10F:
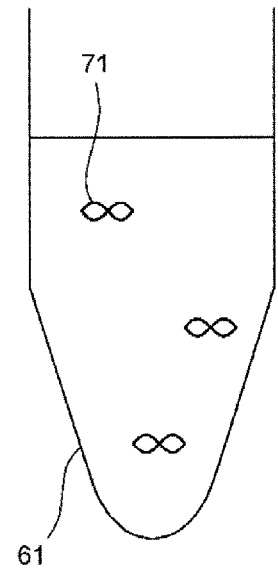

In the third step, the second reagent is dispensed into the elution container 13. As a result, the DNA 71 is released from the magnetic particle 77, and the inside of the elution container 13 exhibits the state shown in FIG. 10E, for example. Subsequently, the magnetic particles 77 are attached to the inner wall of the elution container 13 by the magnet 521 of the elution unit 500 shown in FIG. 5, and the supernatant liquid in the elution container 13 is dispensed into the container 61. At this time, the sample in the container 61 exhibits the state in which unnecessary substance other than the DNA 71 have been removed, as shown in FIG. 10F, for example. Thus, the nucleic acid extracting process performed on one plasma specimen ends.

Next, the first to third steps will be described with reference to FIG. 11 to FIG. 17.

In the flow charts described below, the controller 701 controls the dispensing unit 200, the reaction unit 300, the washing unit 400, and the elution unit 500, whereby the process of each step is performed. As described above, the first to third steps are performed for each plasma specimen for which the process has been started, and thus, in the following, the processes performed on one plasma specimen will be described.

Figure 11:
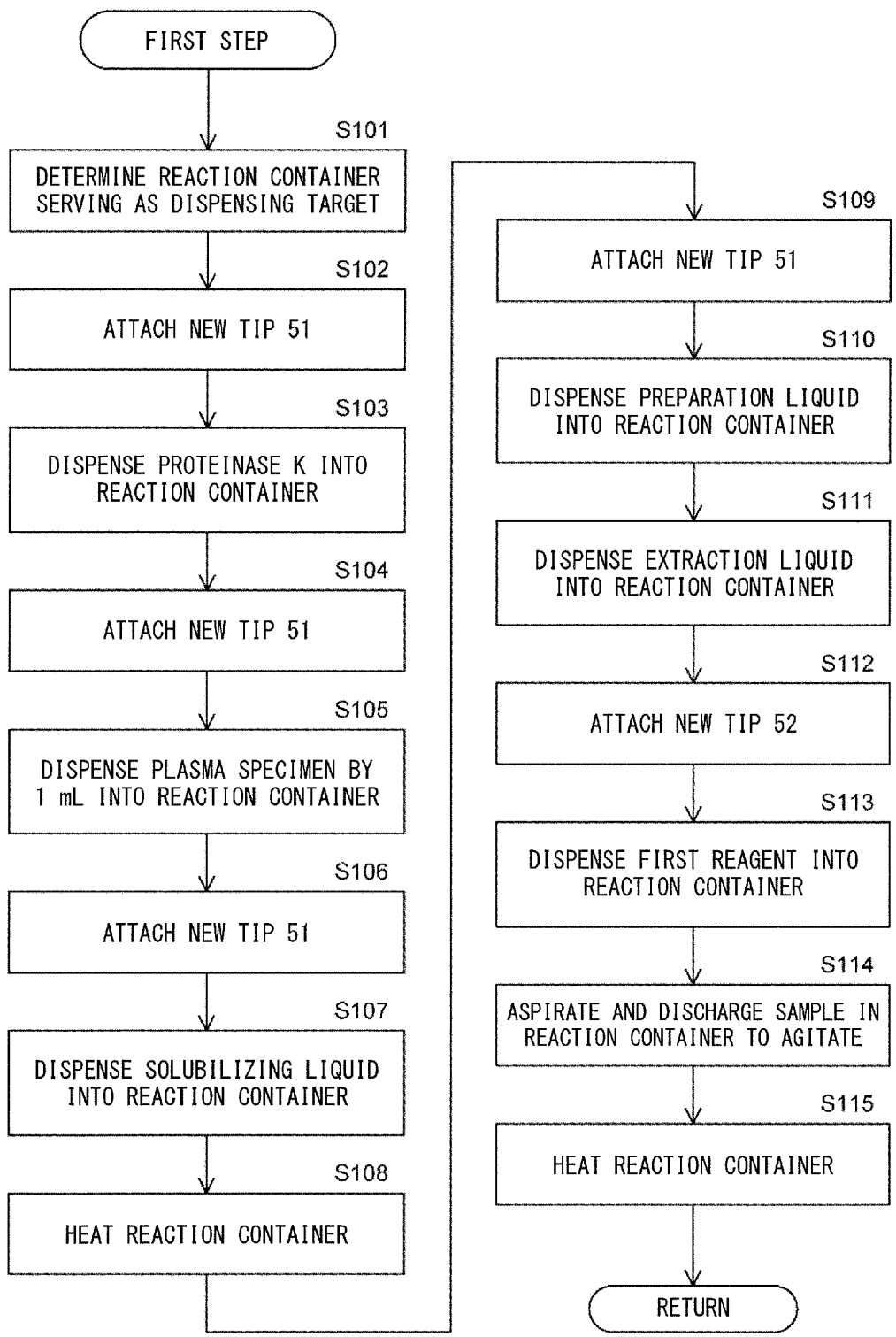
FIG. 11 is a flow chart showing the process of a first step according to the embodiment.

As shown in FIG. 11, in step S101, the controller 701 reads out, from the storage unit 702, plasma specimen amount information that corresponds to the plasma specimen to be processed, and determines the reaction containers as the dispensing target in accordance with the read plasma specimen amount information.

Specifically, when the plasma specimen amount information corresponds to 1 mL, 2 mL, 3 mL, 4 mL, or 5 mL, the number of the reaction containers 11 as the dispensing target is one, two, three, four, or five, respectively. Then, as the dispensing target reaction containers 11, the reaction containers 11 on the Y axis negative side are determined in order, from among the five reaction containers 11 disposed on the plate member 110. For example, when the plasma specimen amount information corresponds to 3 mL, three reaction containers 11 on the Y axis negative side are determined as the dispensing target. Thus, in the process below, among the five reaction containers 11, only the reaction containers 11 determined as the dispensing target will be used in the process. That is, the dispensing process is performed only on the reaction containers 11 determined as the dispensing target.

In step S102, the controller 701 causes a new tip 51 held in the holding member 150 to be attached to the nozzle 201. In step S103, the controller 701 causes proteinase K contained in the reagent container 31 to be dispensed by a predetermined amount into each reaction container 11. In step S104, the controller 701 causes the tip 51 attached to the nozzle 201 to be discarded, and causes a new tip 51 to be attached to the nozzle 201. In step S105, the controller 701 causes the plasma specimen contained in the specimen container 41 to be dispensed by 1 mL into each reaction container 11.

In step S106, the controller 701 causes the tip 51 attached to the nozzle 201 to be discarded, and causes a new tip 51 to be attached to the nozzle 201. In step S107, the controller 701 causes the solubilizing liquid contained in the reagent container 21 to be dispensed by a predetermined amount into each reaction container 11. In step S108, the controller 701 causes the two heaters 311 of the reaction unit 300 to heat each reaction container 11, thereby to heat the sample in each reaction container 11. Accordingly, reaction advances in each reaction container 11, and as described with reference to FIG. 10B, the histone 72 is separated from the DNA 71, and the histone 72, the enzyme 73, and the plasma specimen protein 74 are denatured and degraded.

In step S109, the controller 701 causes the tip 51 attached to the nozzle 201 to be discarded, and causes a new tip 51 to be attached to the nozzle 201. In step S110, the controller 701 causes the preparation liquid contained in the reagent container 22 to be dispensed by a predetermined amount into each reaction container 11. Further, in step S111, the controller 701 causes the extraction liquid contained in the reagent container 23 to be dispensed by a predetermined amount into each reaction container 11.

In step S112, the controller 701 causes the tip 51 attached to the nozzle 201 to be discarded, and causes a new tip 52 to be attached to the nozzle 202. In step S113, the controller 701 causes the first reagent contained in the reagent container 24 to be dispensed by a predetermined amount into each reaction container 11. In step S114, the controller 701 causes, for each reaction container 11, an operation of aspirating and discharging the sample in the reaction container 11 to be consecutively performed, thereby to agitate the sample in the reaction container 11. Hereinafter, this agitating operation will be referred to as "agitation through aspiration/discharge". In step S115, the controller 701 causes the two heaters 311 to heat each reaction container 11, thereby to heat the sample in each reaction container 11. Accordingly, as described with reference to FIG. 10C, the DNA 71 attaches to the magnetic particle 77. Then, the first step ends.

The amount of the plasma specimen and the amounts of the reagents that are dispensed into each reaction container 11 are determined so that reaction in the reaction container 11 can be efficiently performed. From this point of view, in the embodiment, the amount of the plasma specimen to be dispensed into each reaction container 11 is set to 1 mL, and the amounts of the reagents that are dispensed into each reaction container 11 are set to predetermined amounts, respectively. Accordingly, at the time point when the first step ends, each reaction container 11 contains 2.92 mL of the sample.

It should be noted that the dispensing of proteinase K in step S103, dispensing of the plasma specimen in step S105, dispensing of the solubilizing liquid in step S107, and heating in step S108 may not be performed in the above order. These processes may be performed in any order, and may be performed in parallel.

Figure 12:
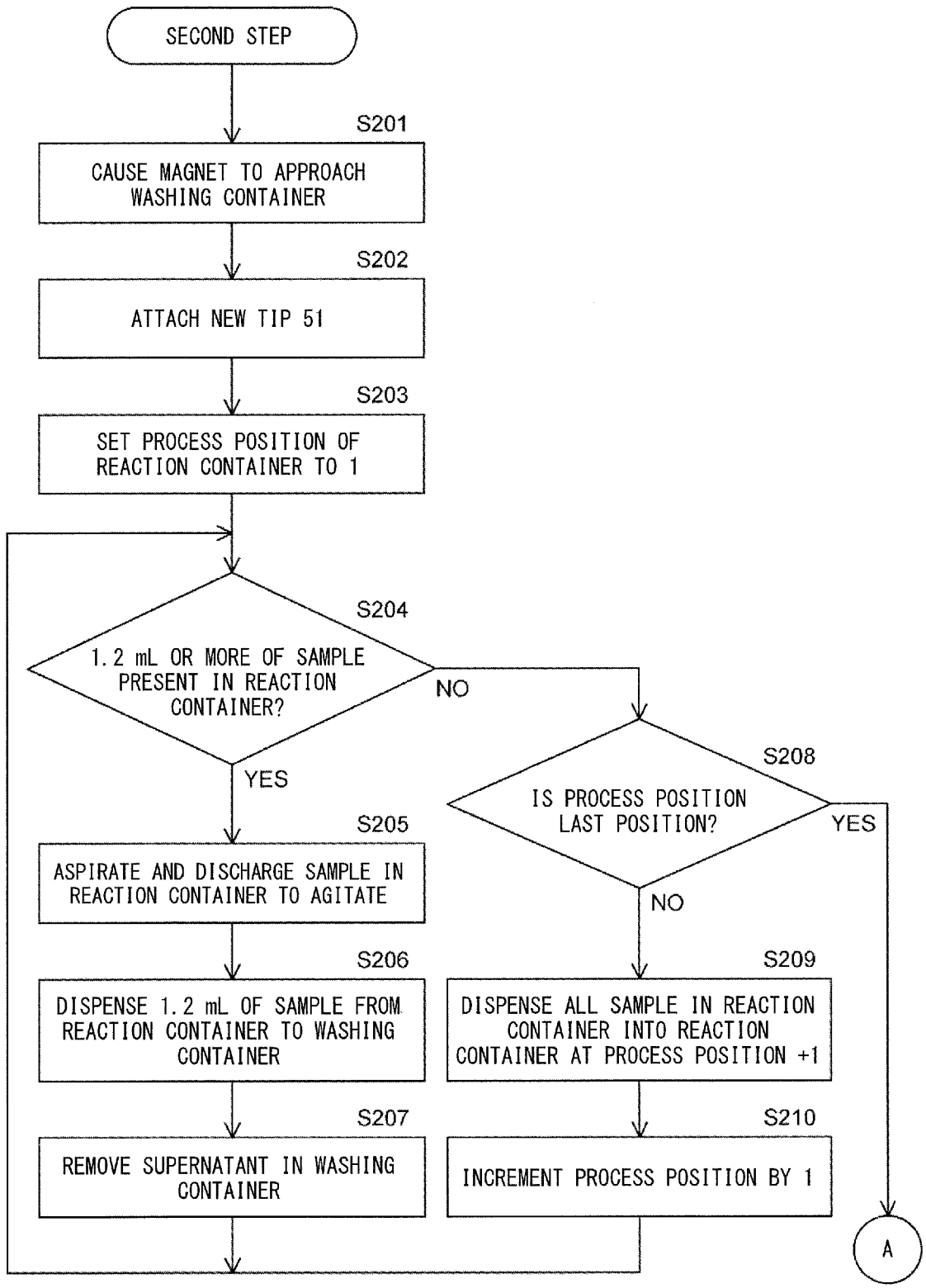
FIG. 12 is a flow chart showing the process of a second step according to the embodiment.

As shown in FIG. 12, in step S201, the controller 701 causes the magnet 411 of the washing unit 400 to approach the washing container 12. In step S202, the controller 701 causes the tip 52 attached to the nozzle 202 to be discarded, and causes a new tip 51 to be attached to the nozzle 201. In step S203, the controller 701 sets the reaction container 11 process position to 1. Accordingly, among the reaction containers 11 as the dispensing target, the position of the reaction container 11 that is located at the Y axis most negative side is set as the process position. The process position is moved one by one to the Y axis positive side in order, being incremented by one in step S210 described later. The value of the process position is stored into the storage unit 702.

In step S204, the controller 701 determines whether 1.2 mL or more of the sample is present in the reaction container 11 at the process position. As described above, at the time point when the first step ends, the amount of the sample contained in each reaction container 11 is 2.92 mL, and the controller 701 has stored in the storage unit 702 the amount of the sample aspirated from each reaction container 11 in step S206 described later. In step S204, on the basis of these pieces of information, the controller 701 determines whether 1.2 mL or more of the sample is present in the reaction container 11 at the process position. It should be noted that the threshold value for the determination in step S204 is set to the maximum amount that can be dispensed at one time via the tip 51.

When the controller 701 has determined that 1.2 mL or more of the sample is present in the reaction container 11 at the process position in step S204, the controller 701 causes the sample contained in the reaction container 11 at the process position to be agitated through aspiration/discharge in step S205. In step S206, the controller 701 causes the sample to be dispensed by 1.2 mL from the reaction container 11 at the process position into the washing container 12. The dispensing amount of the sample in step S206 is set to the maximum amount that can be dispensed at one time via the tip 51. Accordingly, the number of times of dispensing from the reaction container 11 to the washing container 12 can be suppressed to the minimum. As a result of the dispensing in step S206, the magnetic particles 77 in the sample attach to the inner wall of the washing container 12. In step S207, the controller 701 causes the supernatant in the washing container 12, i.e., the supernatant of the sample in the washing container 12, to be aspirated, and causes the aspirated supernatant to be discarded into a discard portion. Then, the controller 701 returns the process to step S204.

When the controller 701 has determined that 1.2 mL or more of the sample is not present in the reaction container 11 at the process position in step S204, then, in step S208, the controller 701 determines whether the process position is the last position. That is, in step S208, the controller 701 determines whether the process position is the position of the reaction container 11 that is located at the Y axis most positive side among the reaction containers 11 as the dispensing target.

When the controller 701 has determined in step S208 that the process position is not the last process position, then, in step S209, the controller 701 causes all the sample contained in the reaction container 11 at the process position to be dispensed into the reaction container 11 at the process position +1. In step S210, the controller 701 increments the value of the process position by one, thereby to move the process position to the Y axis positive side by one. Then, the controller 701 returns the process to step S204. On the other hand, when the controller 701 has determined in step S208 that the process position is the last position, the controller 701 advances the process to step S211 in FIG. 13.

Figure 13:
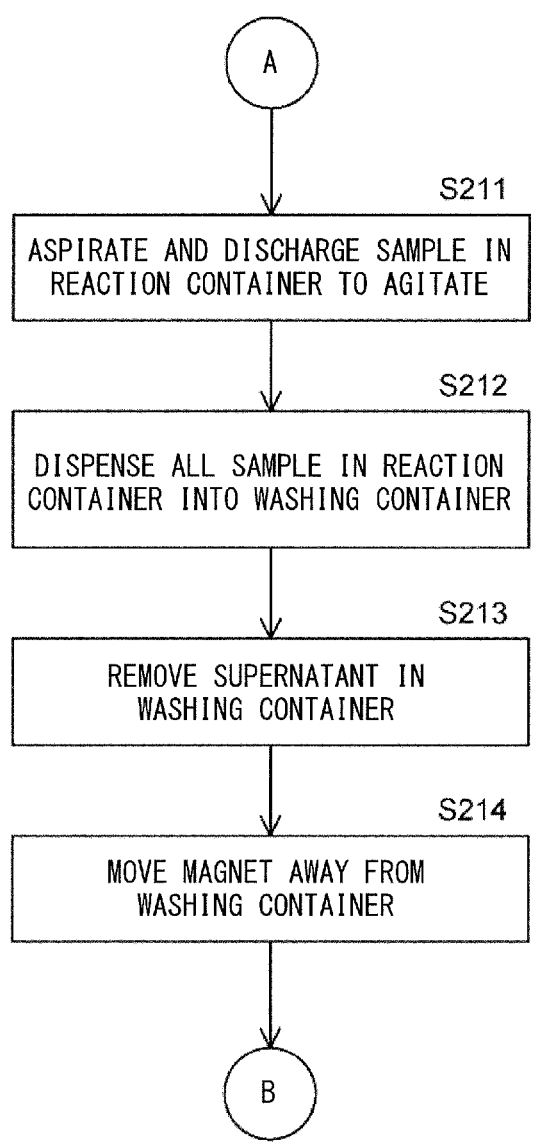
FIG. 13 is a flow chart showing the process of the second step according to the embodiment.

As shown in FIG. 13, in step S211, the controller 701 causes the sample contained in the reaction container 11 at the process position to be agitated through aspiration/discharge. In step S212, the controller 701 causes all the sample contained in the reaction container 11 at the process position to be dispensed into the washing container 12. In step S213, the controller 701 causes the supernatant in the washing container 12 to be removed. In step S214, the controller 701 causes the magnet 411 of the washing unit 400 to be moved away from the washing container 12, and advances the process to step S215 in FIG. 15.

As described above, in the processes of step S201 to S214, a constant amount of the sample is dispensed into the washing container 12 from the reaction container 11 in which reaction has been completed, the magnetic particles are caused to attach the inner wall of the washing container 12, and then, operation of removing the supernatant from the washing container 12 is performed a plurality of times. Accordingly, compared with a case where the sample in each reaction container 11 is transferred at one time into a container having a large capacity and operation of removing the supernatant from this container is performed only once, the supernatant containing unnecessary components can be quickly and reliably removed.

Now, dispensing of the sample performed in steps S203 to S210 in FIG. 12 will be described with reference to FIGS. 14A to 14H. In the example shown in FIGS. 14A to 14H, only two reaction containers 11 on the Y axis negative side are used in the process.

Figure 14A:
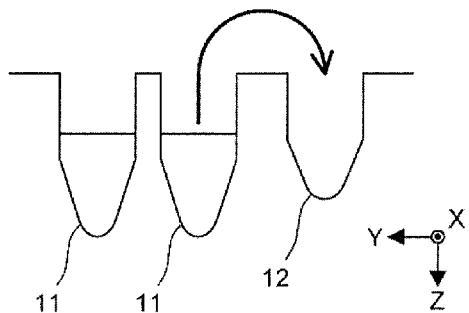
FIG. 14A is a diagram for describing dispensing of a sample performed in the first half of the second step according to the embodiment.
Figure 14B:
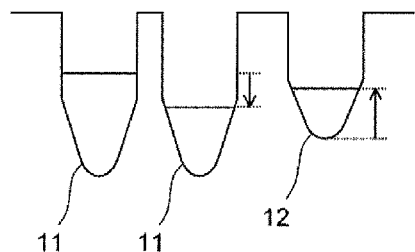
FIG. 14B is a diagram for describing dispensing of the sample performed in the first half of the second step according to the embodiment.

In step S203, the process position is set to 1. In step S204, it is determined that 1.2 mL or more of the sample is present in the reaction container 11 on the Y axis negative side at the process position. Thus, as shown in FIG. 14A, in step S206, 1.2 mL of the sample is dispensed into the washing container 12 from the reaction container 11 on the Y axis negative side at the process position. Accordingly, as shown in FIG. 14B, the liquid amount at the process position is decreased, and the liquid amount in the washing container 12 is increased. Then, in step S207, the supernatant in the washing container 12 is removed, and the process is returned to step S204.

Figure 14C:
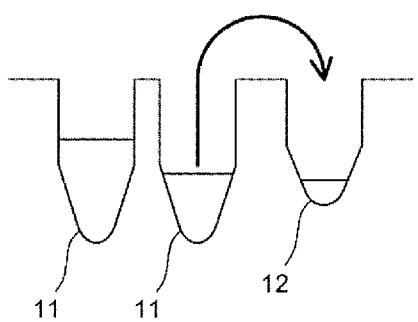
FIG. 14C is a diagram for describing dispensing of the sample performed in the first half of the second step according to the embodiment.
Figure 14D:
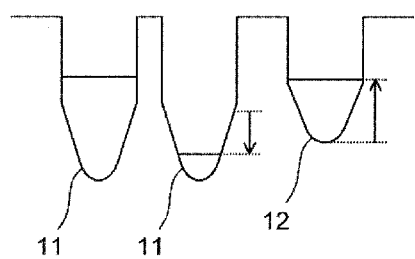
FIG. 14D is a diagram for describing dispensing of the sample performed in the first half of the second step according to the embodiment.

In step S204, it is determined that 1.2 mL or more of the sample is still present in the reaction container 11 on the Y axis negative side at the process position. Thus, as shown in FIG. 14C, dispensing of the sample is performed in step S206, and then, as shown in FIG. 14D, the liquid amount at the process position is decreased and the liquid amount in the washing container 12 is increased. Then, in step S207, the supernatant in the washing container 12 is removed, and the process is returned to step S204.

Figure 14E:
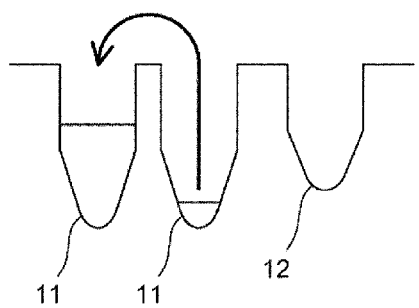
FIG. 14E is a diagram for describing dispensing of the sample performed in the first half of the second step according to the embodiment.

At this time, as shown in FIG. 14E, the sample remains in the reaction container 11 at the process position, by an amount less than 1.2 mL which is the maximum aspiration amount of the tip 51. Here, the sample remains by an amount of 0.52 mL=2.92−1.2×2. As described above, the plasma specimen and the reagents are dispensed into one reaction container 11, by respective amounts that have been determined in advance so that reaction advances efficiently in the reaction container 11. As a result, the reaction container 11 contains 2.92 mL of the sample. In addition, the amount of the sample aspirated from the reaction container 11 is 1.2 mL which is the maximum amount that can be dispensed at one time via the tip 51. Therefore, in the embodiment, when the sample is dispensed from one reaction container 11, a specific amount of the sample remains.

Figure 14F:
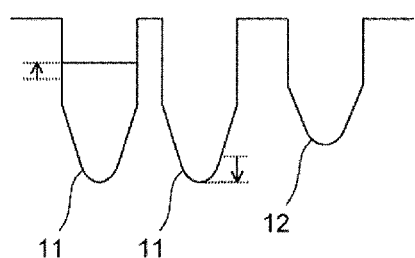
FIG. 14F is a diagram for describing dispensing of the sample performed in the first half of the second step according to the embodiment.

In step S204, it is determined that 1.2 mL or more of the sample is not present in the reaction container 11 on the Y axis negative side at the process position. Then, in step S208, it is determined that the process position is not the last position. Accordingly, as shown in FIG. 14E, in step S209, all the sample contained in the reaction container 11 on the Y axis negative side at the process position is dispensed into the reaction container 11 on the Y axis positive side at the process position +1. Accordingly, as shown in FIG. 14F, the liquid amount of the reaction container 11 at the process position becomes 0, and the liquid amount of the reaction container 11 at the process position +1 is increased. Then, in step S210, the process position is incremented by one, and the process is returned to step S204.

Figure 14G:
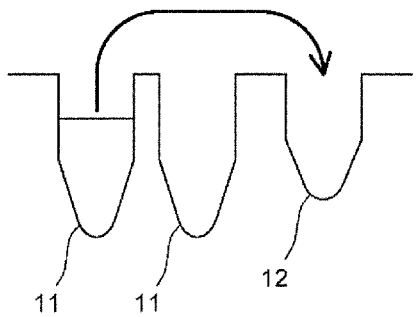
FIG. 14G is a diagram for describing dispensing of the sample performed in the first half of the second step according to the embodiment.
Figure 14H:
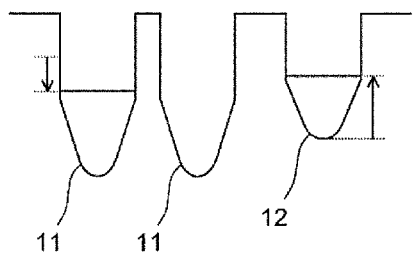
FIG. 14H is a diagram for describing dispensing of the sample performed in the first half of the second step according to the embodiment.

In step S204, it is determined that 1.2 mL or more of the sample is present in the reaction container 11 on the Y axis positive side at the process position. Thus, as shown in FIG. 14G, in step S206, the sample is dispensed by 1.2 mL into the washing container 12 from the reaction container 11 on the Y axis positive side at the process position. Accordingly, as shown in FIG. 14H, the liquid amount at the process position is decreased and the liquid amount of the washing container 12 is increased. In a similar manner, the plasma specimen is dispensed each time by 1.2 mL into the washing container 12 from the reaction container 11 on the Y axis positive side.

Thereafter, when it is determined in step S204 that 1.2 mL or more of the sample is not present in the reaction container 11 on the Y axis positive side at the process position, and then, it is determined in step S208 that the process position is the last position, the process is advanced to step S211. Then, in step S212, all the sample contained in the reaction container 11 on the Y axis positive side at the process position is dispensed into the washing container 12. In this manner, the sample is dispensed into the washing container 12 from each reaction container 11 where reaction has been completed.

As described above, when the amount of the sample present in the reaction container 11 at the process position is less than the constant amount, the sample remaining in the reaction container 11 at the process position is dispensed into the reaction container 11 at the process position +1. This can reduce the number of times of removing the supernatant in the washing container 12, and thus, can shorten the time required in the entire process. In addition, after the sample remaining in the reaction container 11 at the process position is dispensed into the reaction container 11 at the process position +1, dispensing of the sample into the washing container 12 from the reaction container 11 at the process position +1 is performed. Accordingly, when there is a reaction container 11 containing the sample other than the reaction container 11 at the process position +1, compared with a case where dispensing of the sample is moved from the another reaction container 11, the total moving distance of the tip 51 can be shortened. Thus, the time required in the entire process can be shortened.

As described above, at the time point when the second step is started, the amount of the sample contained in each reaction container 11 is 2.92 mL. In the embodiment, each reaction container 11 containing 2.92 mL of the sample is configured to be able to further contain the sample by the constant amount. Specifically, the reaction container 11 according to the embodiment is configured to be able to contain the sample of 4.12 mL=2.92+1.2 mL. Therefore, when it has been determined that the contained sample is less than 1.2 mL, this sample can be contained in one reaction container 11 at the process position +1, without being divided into two portions so as to be contained in two reaction containers 11. Accordingly, the time required in dispensing can be shortened.

It should be noted that when the amount of the sample to be contained in the reaction container 11 and the aspiration amount of the tip 51 are set to values other than the values set in the embodiment, it is conceivable that, in step S206, all the sample at the process position is dispensed into the washing container 12. In this case, unless the process position is the last position, after the process of step S207, the process position is incremented by one, and the process is returned to step S204. Meanwhile, if the process position is the last position, after the process of step S207, the process is advanced to step S214.

Figure 15:
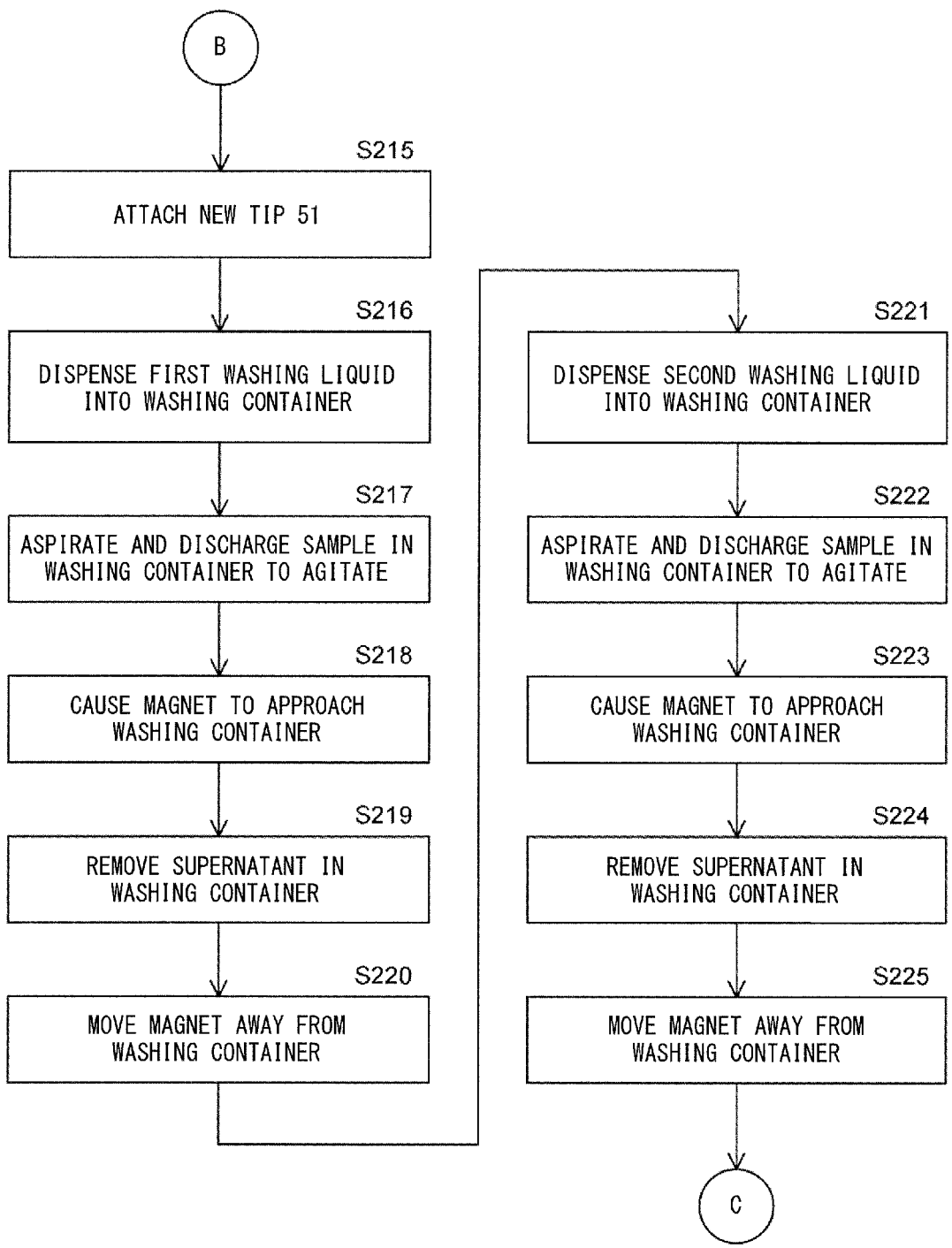
FIG. 15 is a flow chart showing the process of the second step according to the embodiment.

As shown in FIG. 15, in step S215, the controller 701 causes the tip 51 attached to the nozzle 201 to be discarded, and causes a new tip 51 to be attached to the nozzle 201. In step S216, the controller 701 causes the first washing liquid contained in the reagent container 25 to be dispensed by a predetermined amount into the washing container 12. In step S217, the controller 701 causes the sample in the washing container 12 to be agitated through aspiration/discharge. In step S218, the controller 701 causes the magnet 411 of the washing unit 400 to approach the washing container 12. As a result, the magnetic particles 77 in the sample attach to the inner wall of the washing container 12. In step S219, the controller 701 causes the supernatant in the washing container 12 to be removed. Accordingly, washing by the first washing liquid is completed. In step S220, the controller 701 causes the magnet 411 of the washing unit 400 to be moved away from the washing container 12.

In step S221, the controller 701 causes the second washing liquid contained in the reagent container 26 to be dispensed by a predetermined amount into the washing container 12. Then, the controller 701 performs the processes of steps S222 to S225, similarly to the processes of steps S217 to S220. By the removal of the supernatant in step S224, washing by the second washing liquid is completed. By the first washing liquid and the second washing liquid being dispensed, the denatured substances 75, 76 bound to the magnetic particles 77 are separated from the magnetic particles 77 as described with reference to FIG. 10D. By the removal of the supernatant in steps S219 and S224, the denatured substances 75, 76 are removed from the sample.

Figure 16:
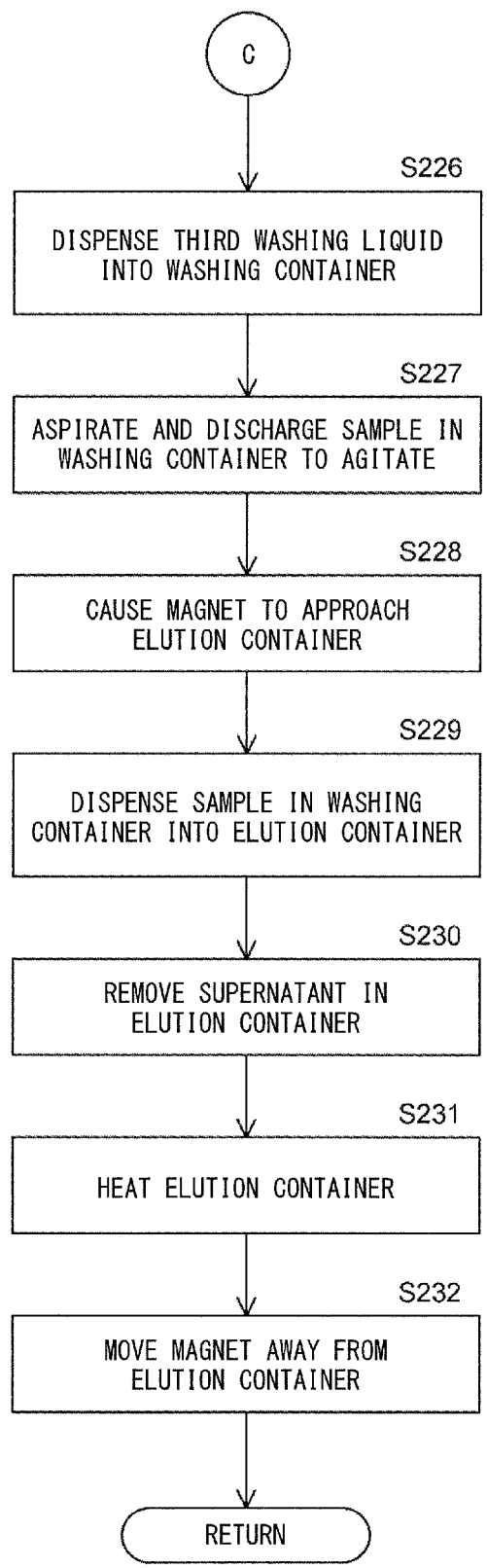
FIG. 16 is a flow chart showing the process of the second step according to the embodiment.

As shown in FIG. 16, in step S226, the controller 701 causes the third washing liquid contained in the reagent container 27 to be dispensed by a predetermined amount into the washing container 12. In step S227, the controller 701 causes the sample in the washing container 12 to be agitated through aspiration/discharge. In step S228, the controller 701 causes the magnet 521 of the elution unit 500 to approach the elution container 13. In step S229, the controller 701 causes the sample contained in the washing container 12 to be dispensed into the elution container 13. That is, the controller 701 causes the sample to be dispensed into the elution container 13 from the washing container 12 in which washing by the first and second washing liquids has been completed.

In step S230, the controller 701 causes the supernatant in the elution container 13 to be removed. Accordingly, washing by the third washing liquid is completed. By the removal of the supernatant in step S230, the denatured substances 75, 76 are removed from the sample. In step S231, the controller 701 causes the heater 511 of the elution unit 500 to heat the elution container 13, thereby to heat the sample in the elution container 13. Accordingly, remaining reagents evaporate from the sample in the elution container 13. In step S232, the controller 701 causes the magnet 521 to be moved away from the elution container 13. Then, the second step ends.

The first to third washing liquids are dispensed into the washing container 12 in a state where the magnet 411 is away from the washing container 12. Accordingly, the sample in the washing container 12 is agitated by the first to third washing liquids, and thus, agitation in the washing container 12 can be more efficiently performed.

Figure 17:
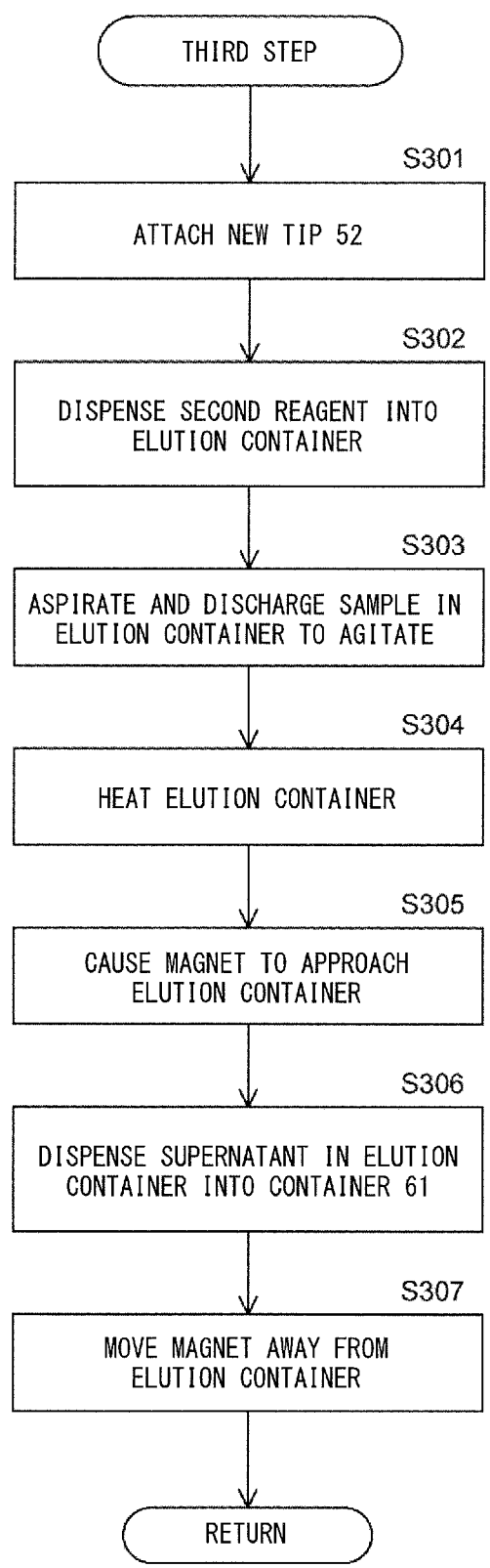
FIG. 17 is a flow chart showing the process of a third step according to the embodiment.

As shown in FIG. 17, in step S301, the controller 701 causes the tip 51 attached to the nozzle 201 to be discarded, and causes a new tip 52 to be attached to the nozzle 202. In step S302, the controller 701 causes the second reagent contained in the reagent container 28 to be dispensed by a predetermined amount into the elution container 13. In step S303, the controller 701 causes the sample in the elution container 13 to be agitated through aspiration/discharge. In step S304, the controller 701 causes the heater 511 of the elution unit 500 to heat the elution container 13, thereby to heat the sample in the elution container 13. Accordingly, reaction in the elution container 13 advances, and the DNA 71 is released from the magnetic particles 77 as described with reference to FIG. 10E.

In step S305, the controller 701 causes the magnet 521 to approach the elution container 13. Accordingly, the magnetic particles 77 in the sample attach to the inner wall of the elution container 13. In step S306, the controller 701 causes the supernatant in the elution container 13 to be dispensed into the container 61. Accordingly, as described with reference to FIG. 10F, the sample in the container 61 exhibits the state in which unnecessary substances other than the DNA 71 have been removed. In step S307, the controller 701 causes the magnet 521 to be moved away from the elution container 13. Thus, the third step ends.

<Modification of Specimen Pretreatment Cartridge>

The specimen pretreatment cartridge 10 may be configured as shown in FIGS. 18A to 18E.

Figure 18A:
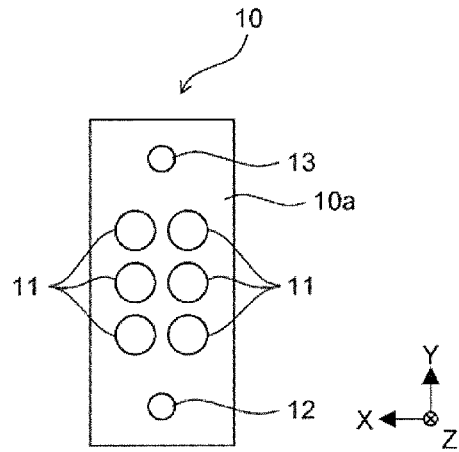
FIG. 18A is a schematic diagram showing a modification of the specimen pretreatment cartridge according to the embodiment.
Figure 18B:
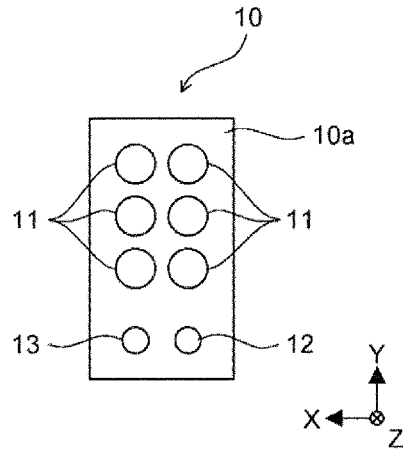
FIG. 18B is a schematic diagram showing a modification of the specimen pretreatment cartridge according to the embodiment.
Figure 18C:
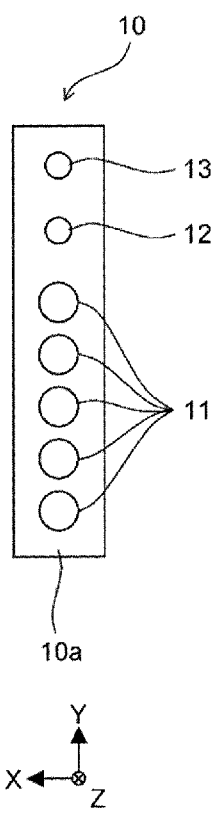
FIG. 18C is a schematic diagram showing a modification of the specimen pretreatment cartridge according to the embodiment.
Figure 18D:
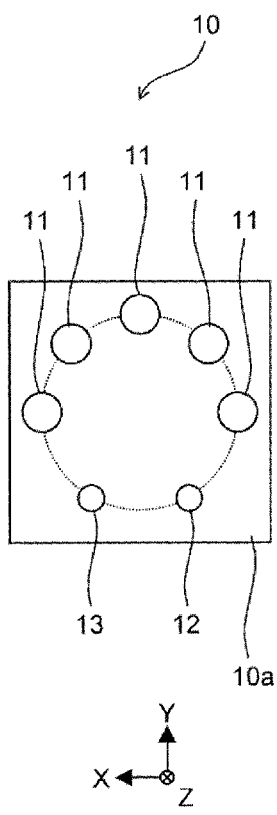
FIG. 18D is a schematic diagram showing a modification of the specimen pretreatment cartridge according to the embodiment.

In the configuration shown in FIG. 18A, compared with the configuration shown in FIG. 1, six reaction containers 11 are provided so as to be arranged in two lines in the Y axis direction, between the washing container 12 and the elution container 13. In the configuration shown in FIG. 18B, compared with the configuration shown in FIG. 1, the washing container 12 and the elution container 13 are formed at an end on the same side of the flat face portion 10a. In addition, to the Y axis positive side of the washing container 12 and the elution container 13, three reaction containers 11 are provided, respectively. In the configuration shown in FIG. 18C, compared with the configuration shown in FIG. 1, the washing container 12 is provided between the elution container 13 and the reaction container 11 on the Y axis positive side. In the configuration shown in FIG. 18D, compared with the configuration shown in FIG. 1, the containers are provided along a circle. In the example shown in FIG. 18E, compared with the configuration shown in FIG. 1, the flat face portion 10a is extended in the Y axis positive direction, and in the extended portion of the flat face portion 10a, the reagent containers 21 to 28 are provided.

In the examples shown in FIGS. 18A, 18B, and 18D, since the containers of the specimen pretreatment cartridge 10 are not arranged in one line, the nozzle 201, 202 needs to be moved also in the X axis direction. However, since the width of the specimen pretreatment cartridge 10 in the Y axis direction is reduced, the setting area in the Y axis direction of the specimen pretreatment apparatus 100 can be reduced.

In the example shown in FIG. 18C, since the washing container 12 is not provided at an end of the specimen pretreatment cartridge 10, the washing unit 400 needs to be set in the X axis direction from the position of the washing container 12 so as to be distanced from the other containers. Similarly, in the example shown in FIG. 18E, since the elution container 13 is not provided at an end of the specimen pretreatment cartridge 10, the elution unit 500 needs to be set in the X axis direction from the position of the elution container 13 so as to be distanced from the other containers. Thus, in the examples shown in FIGS. 18C and 18E, the setting area in the X axis direction of the specimen pretreatment apparatus 100 is increased. Thus, it is preferable that the washing container 12 and the elution container 13 are provided at the end(s) of the specimen pretreatment cartridge 10.

Figure 18E:
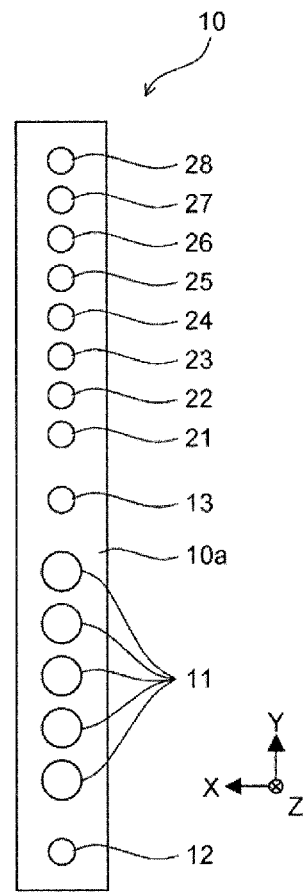
FIG. 18E is a schematic diagram showing a modification of the specimen pretreatment cartridge according to the embodiment.

In the configuration shown in FIG. 18E, since the reagent containers 21 to 28 are provided in the specimen pretreatment cartridge 10, the reagent cartridge 20 shown in FIG. 1 need not be separately prepared. Accordingly, simply by setting one specimen pretreatment cartridge 10, the reaction containers 11, the washing container 12, the elution container 13, and the reagent containers 21 to 28 can be set in the specimen pretreatment apparatus 100.

The specimen pretreatment cartridge 10 shown in FIG. 1 is provided with the washing container 12 and the elution container 13 in order to perform the process of removing impurities contained in the sample and the process of separating DNA from the magnetic particles. However, not limited thereto, the specimen pretreatment cartridge 10 may further include containers in addition to the washing container 12 and the elution container 13, in order to perform removal of impurities and separation of DNA.

What is claimed is:

1. A specimen pretreatment apparatus comprising:
   a dispensing unit configured to dispense a plasma specimen and a first reagent including magnetic particles on which an analyte in the plasma specimen is absorbed;
   a reaction unit including a heating portion that is configured to heat a plurality of reaction containers, the plurality of reaction containers being detachably provided in the reaction unit;
   a washing unit including a magnetic force applying portion that is configured to apply a magnetic force to a washing container, the washing container being detachably provided in the washing unit; and
   a controller programmed to:
      obtain plasma specimen amount information, wherein the plasma specimen amount information refers to an amount of the plasma specimen to be processed;
      determine a number of reaction containers to use based on the obtained plasma specimen amount information;
      control the dispensing unit to dispense the plasma specimen and the first reagent into the determined number of reaction containers of the reaction unit;
      control the heating portion included in the reaction unit to heat the plurality of reaction containers to accelerate a reaction of the plasma specimen and the first reagent contained in each reaction container;
      control the dispensing unit to dispense a mix liquid of the plasma specimen and the first reagent from the plurality of reaction containers into the washing container; and
      control the magnetic force applying portion included in the washing unit to apply the magnetic force to the washing container to remove the magnetic particles contained in the mix liquid.

2. The specimen pretreatment apparatus of claim 1, comprising:
   a second reagent container for containing a second reagent for separating the analyte from the magnetic particles; and
   an elution unit in which an elution container is disposed, wherein the controller is programmed to control the dispensing unit to:
dispense, from the washing container into the elution container, the discharged mix liquid from which the liquid component has been removed, and dispense the second reagent into the elution container.

3. The specimen pretreatment apparatus of claim 1, wherein the reaction unit includes the heating portion that is configured to heat the plurality of reaction containers, the plurality of reaction containers being integrally formed in the specimen pretreatment apparatus.

4. The specimen pretreatment apparatus of claim 1, wherein the controller is programmed to:
obtain, from an input unit, the plasma specimen amount information.

5. The specimen pretreatment apparatus of claim 1, wherein the controller is programmed to control the dispensing unit to dispense an equal amount of the plasma specimen into each reaction container of the determined number of reaction containers.

6. The specimen pretreatment apparatus of claim 1, wherein the controller is further programmed to:
determine an amount of the plasma specimen as compared to a predetermined amount; and
control the dispensing unit to dispense the plasma specimen into a single reaction container of the plurality of reaction containers in response to determining that the amount of the plasma specimen is equal to or less than the predetermined amount.

7. The specimen pretreatment apparatus of claim 1, wherein
the controller is programmed to control the dispensing unit such that the dispensing unit performs:
an operation of dispensing the mix liquid into the washing container from one reaction container among the plurality of reaction containers; and
an operation of removing the liquid component from the washing container while the magnetic particles contained in the discharged mix liquid is attracted by the magnetic force applying portion; wherein
the controller is programmed to control the dispensing unit such that the dispensing unit performs the dispensing operation and the removing operation with respect to each of the other reaction containers among the plurality of reaction containers.

8. The specimen pretreatment apparatus of claim 7, wherein
the dispensing unit is configured to perform the dispensing operation and the removing operation, with a detachable tip attached thereto, and
the controller is programmed to control the dispensing unit such that
the dispensing unit replaces the tip with a new tip after the discharging operation and the removing operation with respect to each of the plurality of reaction containers have been completed, and dispenses a washing liquid into the washing container via the new tip.

9. The specimen pretreatment apparatus of claim 8, wherein
the controller is programmed to control the dispensing unit such that
after performing the dispensing operation of dispensing a constant amount of the mix liquid and the removing operation a plurality of times with respect to the one reaction container, the dispensing unit performs the dispensing operation of dispensing the constant amount of the mix liquid and the dispensing operation a plurality of times with respect to each of the other reaction containers.

10. The specimen pretreatment apparatus of claim 9, wherein
the controller is programmed to control the dispensing unit such that
when an amount of the sample remaining in the one reaction container for which the dispensing operation has been performed is less than the constant amount, the dispensing unit dispenses the sample remaining in the one reaction container into another reaction container for which the dispensing operation is to be performed next.

11. The specimen pretreatment apparatus of claim 10, wherein
the controller is programmed to control the dispensing unit such that
after dispensing the sample remaining in the one reaction container into the another reaction container, the dispensing unit performs the dispensing operation and the aspirating and removing operation with respect to the another reaction container.

12. The specimen pretreatment apparatus of claim 2, wherein
the elution unit includes a heating portion configured to heat the elution container,
the controller is programmed to perform operations comprising:
controlling the dispensing unit so as to dispense the second reagent into the elution container without magnetic force being applied to the elution container;
causing the elution container to be heated without magnetic force being applied to the elution container; and
controlling the dispensing unit such that, after the magnetic particles in the washing container are attracted in a state where magnetic force is applied to the elution container, the dispensing unit aspirates from the elution container the liquid component including the analyte.

13. The specimen pretreatment apparatus of claim 12, wherein
the controller is programmed to control the dispensing unit such that
the dispensing unit dispenses the sample contained in the washing container into the elution container in a state where magnetic force is applied to the elution container, and removes the liquid component in the sample in a state where the magnetic particles contained in the dispensed sample are attracted by the magnetic force applying portion.

14. The specimen pretreatment apparatus of claim 12, wherein
the heating portion includes a heater, and a conductive member configured to conduct heat of the heater to the elution container,
the magnetic force applying portion includes a magnet, and a magnet driving portion configured to move the magnet;
the conductive member includes an elution container holder configured to hold the elution container, and a hole continued to the elution container holder; and the magnet driving portion is configured to be able to move the magnet along the hole.

\* \* \* \* \*